(12) United States Patent
Ishitani

(10) Patent No.: US 11,878,279 B2
(45) Date of Patent: Jan. 23, 2024

(54) ELECTROCHEMICAL REDUCTION OF CARBON DIOXIDE

(71) Applicant: JAPAN SCIENCE AND TECHNOLOGY AGENCY, Kawaguchi (JP)

(72) Inventor: Osamu Ishitani, Meguro-ku (JP)

(73) Assignee: JAPAN SCIENCE AND TECHNOLOGY AGENCY, Kawaguchi (JP)

( * ) Notice: Subject to any disclaimer, the term of this patent is extended or adjusted under 35 U.S.C. 154(b) by 0 days.

(21) Appl. No.: 17/835,021

(22) Filed: Jun. 8, 2022

(65) Prior Publication Data

US 2022/0305474 A1    Sep. 29, 2022

Related U.S. Application Data

(60) Division of application No. 16/887,389, filed on May 29, 2020, now abandoned, which is a continuation of
(Continued)

(30) Foreign Application Priority Data

Feb. 27, 2015 (JP) ................................. 2015-037839
Aug. 18, 2015 (JP) ................................. 2015-160768

(51) Int. Cl.
   *C25B 1/00* (2021.01)
   *B01J 31/22* (2006.01)
   (Continued)

(52) U.S. Cl.
   CPC ....... *B01J 31/2217* (2013.01); *B01J 31/0244* (2013.01); *B01J 31/22* (2013.01);
   (Continued)

(58) Field of Classification Search
   None
   See application file for complete search history.

(56) References Cited

U.S. PATENT DOCUMENTS 4,608,133 A    8/1986    Morduchowitz
4,711,708 A    12/1987   Meyer et al.
(Continued)

FOREIGN PATENT DOCUMENTS

CN    101910469 A    12/2010
CN    102190573 A    9/2011
(Continued)

OTHER PUBLICATIONS

International Search Report dated May 17, 2016 in PCT/JP2016/053558 filed Feb. 5, 2016.
(Continued)

*Primary Examiner* — Yun Qian
(74) *Attorney, Agent, or Firm* — Oblon, McClelland, Maier & Neustadt, L.L.P.

(57) ABSTRACT

Disclosed herein is a method for selectively reducing, using electrical energy, $CO_2$ to formic acid, a catalyst for use in the method, and an electrochemical reduction system. The method for producing formic acid by electrochemically reducing carbon dioxide of the present invention includes (a) reacting carbon dioxide with a metal complex represented
(Continued)

- SCHEMATIC DIAGRAM OF ELECTROCHEMICAL CELL -

1 SOLUTION CONTAINING COMPLEX MOLECULE
2 GAS INJECTION PORT
3 GAS DISCHARGE PORT
4 WORKING ELECTRODE
5 REFERENCE ELECTRODE
6 COUNTER ELECTRODE
7 ION EXCHANGE MEMBRANE
8 POTENTIOSTAT by formula (1), and (b) applying a voltage to a reaction product of the carbon dioxide and the metal complex represented by formula (1):

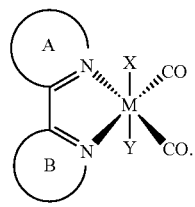

(1)

5 Claims, 13 Drawing Sheets

Related U.S. Application Data application No. 15/553,739, filed as application No. PCT/JP2016/053558 on Feb. 5, 2016, now abandoned.

(51) Int. Cl.

| | | |
|---|---|---|
| C07F 13/00 | (2006.01) | |
| C25B 3/25 | (2021.01) | |
| C25B 9/19 | (2021.01) | |
| C07D 213/22 | (2006.01) | |
| C07D 213/06 | (2006.01) | |
| C07D 213/68 | (2006.01) | |
| C01B 32/40 | (2017.01) | |
| B01J 31/02 | (2006.01) | |
| C07C 53/02 | (2006.01) | |
| C07D 241/36 | (2006.01) | |
| G01N 30/02 | (2006.01) | |
| B01J 31/20 | (2006.01) | |
| G01N 30/88 | (2006.01) | |
| B01J 31/18 | (2006.01) | |
| G01N 21/35 | (2014.01) | |

(52) U.S. Cl.
CPC ............. *C01B 32/40* (2017.08); *C07C 53/02* (2013.01); *C07D 213/06* (2013.01); *C07D 213/22* (2013.01); *C07D 213/68* (2013.01); *C07D 241/36* (2013.01); *C07F 13/00* (2013.01); *C25B 1/00* (2013.01); *C25B 3/25* (2021.01); *C25B 9/19* (2021.01); *B01J 31/1815* (2013.01); *B01J 31/20* (2013.01); *B01J 31/2204* (2013.01); *B01J 2531/72* (2013.01); *B01J 2531/74* (2013.01); *G01N 21/35* (2013.01); *G01N 2030/025* (2013.01); *G01N 2030/884* (2013.01)

(56) References Cited

U.S. PATENT DOCUMENTS

| | | | |
|---|---|---|---|
| 5,384,299 A | 1/1995 | Turner et al. | |
| 2013/0277209 A1* | 10/2013 | Sato | C25B 11/057 |
| | | | 204/252 |
| 2014/0034506 A1 | 2/2014 | Kyle et al. | |

FOREIGN PATENT DOCUMENTS

| | | |
|---|---|---|
| CN | 103140608 A | 6/2013 |
| JP | 2004-217632 A | 8/2004 |
| JP | 2011-82144 A | 4/2011 |
| JP | 2011-94194 A | 5/2011 |
| JP | 2013-180943 A | 9/2013 |
| JP | 2013-193056 A | 9/2013 |
| JP | 2014-62038 A | 4/2014 |
| KR | 10-2013-0085635 A1 | 7/2013 |
| WO | WO 2010/009273 A1 | 1/2010 |
| WO | WO 2012/015905 A1 | 2/2012 |
| WO | WO 2012/091045 A1 | 7/2012 |

OTHER PUBLICATIONS

Tatsuko Morimoto, et al., "$CO_2$ Capture by a Rhenium(I) Complex with the Aid of Teirthanolamine" Journal of the American Chemical Society, vol. 135, 2013, pp. 16825-16828.

Hisao Hori, et al., "Efficient photocatalytic $CO_2$ reduction using [Re(bpy)(CO)$_3$ {P(OEt)$_3$}]" Journal or Photochemistry and Photobiology A: Chemistry, vol. 96, 1996, pp. 171-174.

Kohel Okamoto, et al., "Photocatalytic $CO_2$ Reduction Using Manganese (I) Bipyridine Carbonyl Complexes with Phosphorous Ligands" 94 Annual Meeting of the Chemical Socirty of Japan (2104), Preprint II, 2014, 5 Pages (with English language translation).

Gerard J. Stor, et al., "The Remarkable Photochemistry of fac-XMn(CO)$_3$(α-diimine) (X=Halide): Formation of Mn$_2$(CO)$_6$(α-diimine)$_2$ via the mer Isomer and Photocatalytic Substitution of X in the Presence of PR3" Organometallics, vol. 13, No. 7, 1994, pp. 2641-2650.

Katsuaki Kobayashi, et al., "Selective Generation of Formamides through Photocatalytic $CO_2$ Reduction Catalyzed by Ruthenium Carbonyl Compounds" Angewandte Chemie International Edition, vol. 53, 2014, pp. 11813-11817.

Johnson et al, *Organometallics*, 15, 3374-3387 (1996).

Office Action dated Sep. 5, 2018 in Chinese Patent Application No. 201680011937.6.

Frank P. A. Johnson, et al., "Electrocatalytic Reduction of $CO_2$ Using the Complexes [Re(bpy)(CO)$_3$L]$^n$ (n=+1, L=P(OEt)$_3$ CH$_3$CN; n=0, L=Cl; Otf; bpy=2,2'Bipyridine; Otf=CF$_3$SO$_3$ as Catalyst Precursors: Infrared Spectroelectrochemical Investigation", Organometallics, Jul. 1, 1996, 15 (15), pp. 3374-3387.

Second Office Action dated Apr. 22, 2019, in Chinese Patent Application No. 201 68001193 7. 6 (with machines translation).

Guo Shucai , Coal Chemical Engineering , Edition 1, Metallurgical Industry Press Co ., Ltd. , Feb. 28, 1991, pp. 259-260.

\* cited by examiner

ELECTROCHEMICAL REDUCTION OF CARBON DIOXIDE

CROSS REFERENCE TO RELATED APPLICATIONS

This application is a divisional application of prior U.S. application Ser. No. 16/887,389, filed May 29, 2020, now pending, the disclosure of which is incorporated herein by reference in its entirety. U.S. application Ser. No. 16/887,389 is a continuation application of prior U.S. application Ser. No. 15/553,739, filed Aug. 25, 2017, now abandoned, the disclosure of which is incorporated herein by reference in its entirety. U.S. application Ser. No. 15/553,739 is the National Stage of PCT/JP2016/053558, filed Feb. 5, 2016, the disclosure of which is incorporated herein by reference in its entirety. This application claims priority to Japanese Application No. 2015-037839, filed Feb. 27, 2015, and Japanese Application No. 2015-160768, filed Aug. 18, 2015, the disclosures of which are incorporated herein by reference in their entireties.

TECHNICAL FIELD

The present invention relates to a method for electrochemically reducing carbon dioxide to carbon monoxide or formic acid, and relates to a catalyst used therefor.

BACKGROUND ART

Currently, people are facing serious problems of global warming and exhaustion of carbon resources. As means for solving these problems, a catalyst for converting light energy into chemical energy is attracting attention. It is expected that these problems should be solved all at once if carbon dioxide ($CO_2$) could be converted into a useful compound using inexhaustible solar energy. $CO_2$ is, however, an end product of oxidation of carbon compounds, and hence is both physically and chemically very stable and has very low reactivity.

Recently, some techniques for converting $CO_2$ into a useful compound through reduction have been reported. For example, Patent Literature 1 describes a method for obtaining formic acid by reacting $CO_2$ and hydrogen in the presence of a catalyst, and Patent Literature 2 describes a method for obtaining formic acid through reduction of $CO_2$ caused by transferring, to a catalyst, an excited electron generated through light irradiation of a semiconductor electrode. Besides, Patent Literature 3 and Non Patent Literature 1 have reported a method for reducing $CO_2$ to carbon monoxide by bringing a rhenium complex into contact with $CO_2$ and irradiating the resultant with light. Furthermore, attempts have been made to electrochemically reducing $CO_2$ in the presence of a metal complex catalyst (Patent Literature 4).

CITATION LIST

Patent Literature

[Patent Literature 1] JP-A-2004-217632
[Patent Literature 2] JP-A-2011-82144
[Patent Literature 3] JP-A-2013-180943
[Patent Literature 4] JP-A-2013-193056

Non Patent Literature

[Non Patent Literature 1] J. Am. Chem. Soc. 2013, 135, 16825-16828

SUMMARY OF INVENTION

Technical Problem

The methods described in Patent Literatures 1 and 2 require, however, hydrogen or a semiconductor and light irradiation for the reduction, and in addition, hydrogen is necessary for the reduction in Patent Literature 1, and thus these methods cannot be said energetically advantageous. Besides, in Patent Literature 3 and Non Patent Literature 1, another catalyst such as a ruthenium complex is necessary for a photocatalytic reaction in addition to a reduction catalyst. Furthermore, in Patent Literature 4, a product resulting from the electrochemical treatment of $CO_2$ is unknown.

On the other hand, if carbon monoxide (CO) or formic acid can be selectively obtained through the reduction of $CO_2$, the thus obtained carbon monoxide can be a material of extremely various hydrocarbons. A hydrocarbon is a chemical energy material similarly to petroleum. Besides, formic acid can be used for easily producing hydrogen through a reaction with a catalyst, and hence is expected as a liquid fuel which stores hydrogen.

Accordingly, an object of the present invention is to provide a method for reducing $CO_2$ selectively to carbon monoxide or formic acid by using electrical energy, a catalyst for use in the method, and an electrochemical reduction system.

Solution to Problem

Therefore, the present inventor made various examinations for electrochemically performing reduction of $CO_2$ to carbon monoxide or formic acid, and found that $CO_2$ can be selectively and easily reduced to carbon monoxide or formic acid by reacting $CO_2$ with a metal complex represented by formula (1) or formula (2) and applying a voltage to the resultant reaction product, and that this reduction reaction proceeds even if the concentration of $CO_2$ to be introduced is low, resulting in accomplishing the present invention.

Specifically, the present invention provides the following [1] to [30]:

[1] A method for producing carbon monoxide by electrochemically reducing carbon dioxide, comprising the following steps (a) and (b):

(a) reacting carbon dioxide with a metal complex represented by formula (1):

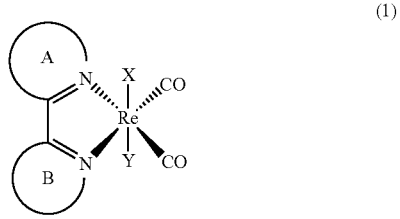

(1)

wherein

X represents $OR^1$, $SR^1$, $NR^2R^3R^4$ or $PX^1X^2X^3$,

Y represents CO, $OR^1$, $SR^1$, $NR^2R^3R^4$ or $PX^1X^2X^3$, ring A and ring B are identical or different and represent a nitrogen atom-containing heterocycle optionally having a substituent, $R^1$ represents a hydrocarbon group optionally having a substituent, one, two or three of $R^2$, $R^3$ and $R^4$ are identical or different and represent a hydrocarbon group optionally having a substituent, the rest representing a hydrogen atom, and one, two or three of $X^1$, $X^2$ and $X^3$ are identical or different and represent a hydrocarbon group optionally having a substituent or a hydrocarbon oxy group optionally having a substituent, the rest representing a hydrogen atom or a hydroxy group; and (b) applying a voltage to a reaction product of the carbon dioxide and the metal complex represented by formula (1).

[2] The production method according to [1], wherein the aforementioned steps (a) and (b) are performed within an electrochemical cell including a working electrode and a counter electrode, and the method comprises the following steps (a1) and (b1):

(a1) introducing carbon dioxide into a solution containing the metal complex held in the electrochemical cell; and (b1) applying a negative voltage and a positive voltage respectively to the working electrode and the counter electrode of the electrochemical cell.

[3] The production method according to [2], wherein the carbon dioxide is introduced by introducing a carbon dioxide-containing gas into the solution containing the metal complex.

[4] The production method according to any one of [1] to [3], wherein the carbon dioxide to be reacted is a gas containing 0.03 to 100% of carbon dioxide.

[5] The production method according to any one of [1] to [4], wherein the nitrogen atom-containing heterocycle including ring A and ring B is a heterocycle having a 2,2'-bipyridine structure optionally having a substituent.

[6] The production method according to any one of [1] to [5], wherein each hydrocarbon group optionally having a substituent represented by $R^1$, $R^2$, $R^3$, $R^4$, $X^1$, $X^2$ and $X^3$ is one selected from the group consisting of an alkyl group, an alkenyl group, a cycloalkyl group, a cycloalkenyl group and an aromatic hydrocarbon group, each of which optionally has one to three substituents selected from the group consisting of a primary, secondary or tertiary amino group, a hydroxy group, an alkoxy group, an aryloxy group, a halogen atom, a nitro group, a cyano group, a formyl group, an alkanoyl group and an arylcarbonyl group.

[7] A method for producing carbon monoxide from carbon dioxide, wherein the carbon monoxide obtained by the production method according to any one of [1] to [6] is used as a reducing agent.

[8] A method for producing a hydrocarbon-based compound, wherein the carbon monoxide obtained by the production method according to any one of [1] to [6] is used as a raw material.

[9] A catalyst for electrochemically reducing carbon dioxide to carbon monoxide, represented by formula (1):

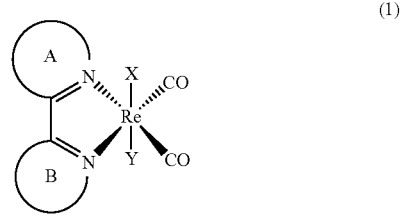

(1)

wherein

X represents $OR^1$, $SR^1$, $NR^2R^3R^4$ or $PX^1X^2X^3$,

Y represents CO, $OR^1$, $SR^1$, $NR^2R^3R^4$ or $PX^1X^2X^3$, ring A and ring B are identical or different and represent a nitrogen atom-containing heterocycle optionally having a substituent, $R^1$ represents a hydrocarbon group optionally having a substituent, one, two or three of $R^2$, $R^3$ and $R^4$ are identical or different and represent a hydrocarbon group optionally having a substituent, the rest representing a hydrogen atom, and one, two or three of $X^1$, $X^2$ and $X^3$ are identical or different and represent a hydrocarbon group optionally having a substituent or a hydrocarbon oxy group optionally having a substituent, the rest representing a hydrogen atom or a hydroxy group.

[10] The catalyst according to [9], wherein the nitrogen atom-containing heterocycle including ring A and ring B is a heterocycle having a 2,2'-bipyridine structure optionally having a substituent.

[11] The catalyst according to [9] or [10], wherein each hydrocarbon group optionally having a substituent represented by $R^1$, $R^2$, $R^3$, $R^4$, $X^2$, $X^2$ and $X^3$ is one selected from the group consisting of an alkyl group, an alkenyl group, a cycloalkyl group, a cycloalkenyl group and an aromatic hydrocarbon group, each of which optionally has one to three substituents selected from the group consisting of a primary, secondary or tertiary amino group, a hydroxy group, an alkoxy group, an aryloxy group, a halogen atom, a nitro group, a cyano group, a formyl group, an alkanoyl group and an arylcarbonyl group.

[12] A method for producing formic acid by electrochemically reducing carbon dioxide, comprising the following steps (a) and (b):

(a) reacting carbon dioxide with a metal complex represented by formula (2):

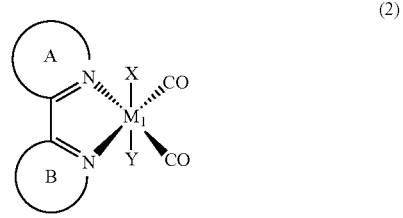

(2)

wherein $M_1$ represents manganese, ruthenium or iron,

X represents $OR^1$, $SR^1$, $NR^2R^3R^4$ or $PX^1X^2X^3$,

Y represents CO, $OR^1$, $SR^1$, $NR^2R^3R^4$ or $PX^1X^2X^3$, ring A and ring B are identical or different and represent a nitrogen atom-containing heterocycle optionally having a substituent, $R^1$ represents a hydrocarbon group optionally having a substituent, one, two or three of $R^2$, $R^3$ and $R^4$ are identical or different and represent a hydrocarbon group optionally having a substituent, the rest representing a hydrogen atom, and one, two or three of $X^1$, $X^2$ and $X^3$ are identical or different and represent a hydrocarbon group optionally having a substituent or a hydrocarbon oxy group optionally having a substituent, the rest representing a hydrogen atom or a hydroxy group; and (b) applying a voltage to a reaction product of the carbon dioxide and the metal complex represented by formula (2).

[13] The production method according to [12], wherein the aforementioned steps (a) and (b) are performed within an electrochemical cell including a working electrode and a counter electrode, and the method comprises the following steps (a1) and (b1): (a1) introducing carbon dioxide into a solution containing the metal complex held in the electrochemical cell; and (b1) applying a negative voltage and a positive voltage respectively to the working electrode and the counter electrode of the electrochemical cell.

[14] The production method according to [13], wherein the carbon dioxide is introduced by introducing a carbon dioxide-containing gas into the solution containing the metal complex.

[15] The production method according to any one of [12] to [14], wherein the carbon dioxide to be reacted is a gas containing 0.03 to 100% of carbon dioxide.

[16] The production method according to any one of [12] to [15], wherein the nitrogen atom-containing heterocycle including ring A and ring B is a heterocycle having a 2,2'-bipyridine structure optionally having a substituent.

[17] The production method according to any one of [12] to [16], wherein each hydrocarbon group optionally having a substituent represented by $R^1$, $R^2$, $R^3$, $R^4$, $X^1$, $X^2$ and $X^3$ is one selected from the group consisting of an alkyl group, an alkenyl group, a cycloalkyl group, a cycloalkenyl group and an aromatic hydrocarbon group, each of which optionally has one to three substituents selected from the group consisting of a primary, secondary or tertiary amino group, a hydroxy group, an alkoxy group, an aryloxy group, a halogen atom, a nitro group, a cyano group, a formyl group, an alkanoyl group and an arylcarbonyl group.

[18] A catalyst for electrochemically reducing carbon dioxide to formic acid, represented by formula (2):

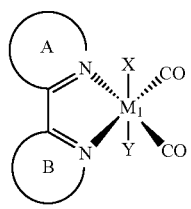

(2)

wherein
$M_1$ represents manganese, ruthenium or iron,
X represents $OR^1$, $SR^1$, $NR^2R^3R^4$ or $PX^1X^2X^3$,
Y represents CO, $OR^1$, $SR^1$, $NR^2R^3R^4$ or $PX^1X^2X^3$,
ring A and ring B are identical or different and represent a nitrogen atom-containing heterocycle optionally having a substituent,
$R^1$ represents a hydrocarbon group optionally having a substituent, one, two or three of $R^2$, $R^3$ and $R^4$ are identical or different and represent a hydrocarbon group optionally having a substituent, the rest representing a hydrogen atom, and one, two or three of $X^1$, $X^2$ and $X^3$ are identical or different and represent a hydrocarbon group optionally having a substituent or a hydrocarbon oxy group optionally having a substituent, the rest representing a hydrogen atom or a hydroxy group.

[19] The catalyst according to [18], wherein the nitrogen atom-containing heterocycle including ring A and ring B is a heterocycle having a 2,2'-bipyridine structure optionally having a substituent.

[20] The catalyst according to [18] or [19], wherein each hydrocarbon group optionally having a substituent represented by $R^1$, $R^2$, $R^3$, $R^4$, $X^1$, $X^2$ and $X^3$ is one selected from the group consisting of an alkyl group, an alkenyl group, a cycloalkyl group, a cycloalkenyl group and an aromatic hydrocarbon group, each of which optionally has one to three substituents selected from the group consisting of a primary, secondary or tertiary amino group, a hydroxy group, an alkoxy group, an aryloxy group, a halogen atom, a nitro group, a cyano group, a formyl group, an alkanoyl group and an arylcarbonyl group.

[21] A metal complex represented by formula (2a):

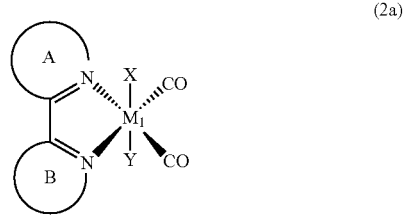

(2a)

wherein
$M_1$ represents manganese, ruthenium or iron,
X represents $O(CH_2)_nNR^5R^6$, $NR^1R^6$ or $PX^1X^2X^3$,
Y represents CO, $O(CH_2)_nNR^5R^6$, $NR^5R^6$ or $PX^1X^2X^3$,
ring A and ring B are identical or different and represent a nitrogen atom-containing heterocycle optionally having a substituent, one, two or three of $X^1$, $X^2$ and $X^3$ are identical or different and represent a hydrocarbon group optionally having a substituent or a hydrocarbon oxy group optionally having a substituent, the rest representing a hydrogen atom or a hydroxy group, $R^5$ and $R^6$ are identical or different and represent an alkyl group, a hydroxyalkyl group or a hydrogen atom, and n represents a number of 2 to 8.

[22] The metal complex according to [21], wherein the nitrogen atom-containing heterocycle including ring A and ring B is a heterocycle having a 2,2'-bipyridine structure optionally having a substituent.

[23] The metal complex according to [21] or [22], wherein each hydrocarbon group optionally having a substituent represented by $X^1$, $X^2$ and $X^3$ is one selected from the group consisting of an alkyl group, an alkenyl group, a cycloalkyl group, a cycloalkenyl group and an aromatic hydrocarbon group, each of which optionally has one to three substituents selected from the group consisting of a primary, secondary or tertiary amino group, a hydroxy group, an alkoxy group, an aryloxy group, a halogen atom, a nitro group, a cyano group, a formyl group, an alkanoyl group and an arylcarbonyl group.

[24] A carbon monoxide production system for producing carbon monoxide by electrochemically reducing carbon dioxide, the carbon monoxide production system comprising:

an electrochemical cell part equipped with a solution containing a metal complex, a working electrode and a counter electrode;

an injection part through which carbon dioxide is injected into the solution containing the metal complex held in the electrochemical cell part;

a voltage source capable of applying a positive or negative voltage between the working electrode and the counter electrode of the electrochemical cell part; and a discharge part discharging carbon monoxide generated within the solution containing the metal complex, wherein the carbon monoxide is generated by applying a positive or negative voltage to a reaction product of the metal complex generated by the solution containing the metal complex and the carbon dioxide.

[25] The carbon monoxide production system according to [24], wherein the metal complex is represented by formula (1):

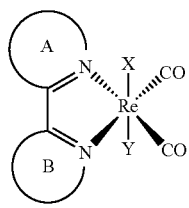

(1)

wherein

X represents $OR^1$, $SR^1$, $NR^2R^3R^4$ or $PX^1X^2X^3$,

Y represents CO, $OR^1$, $SR^1$, $NR^2R^3R^4$ or $PX^1X^2X^3$, ring A and ring B are identical or different and represent a nitrogen atom-containing heterocycle optionally having a substituent, $R^1$ represents a hydrocarbon group optionally having a substituent, one, two or three of $R^1$, $R^3$ and $R^4$ are identical or different and represent a hydrocarbon group optionally having a substituent, the rest representing a hydrogen atom, and one, two or three of $X^1$, $X^2$ and $X^3$ are identical or different and represent a hydrocarbon group optionally having a substituent or a hydrocarbon oxy group optionally having a substituent, the rest representing a hydrogen atom or a hydroxy group.

[26] The carbon monoxide production system according to [24] or [25], wherein the carbon dioxide is fed without concentration in a feed part feeding the carbon dioxide.

[27] The carbon monoxide production system according to any one of [24] to [26], further comprising a carbon monoxide detection part detecting a concentration of the carbon monoxide discharged from the solution containing the metal complex.

[28] The carbon monoxide production system according to [27], wherein the carbon monoxide detection part is a gas chromatography.

[29] The carbon monoxide production system according to any one of [24] to [28], wherein the nitrogen atom-containing heterocycle including ring A and ring B is a heterocycle having a 2,2'-bipyridine structure optionally having a substituent.

[30] The carbon monoxide production system according to any one of [24] to [29], wherein each hydrocarbon group optionally having a substituent represented by $R^1$, $R^2$, $R^3$, $R^4$, $X^1$, $X^2$ and $X^3$ is one selected from the group consisting of an alkyl group, an alkenyl group, a cycloalkyl group, a cycloalkenyl group and an aromatic hydrocarbon group, each of which optionally has one to three substituents selected from the group consisting of a primary, secondary or tertiary amino group, a hydroxy group, an alkoxy group, an aryloxy group, a halogen atom, a nitro group, a cyano group, a formyl group, an alkanoyl group and an arylcarbonyl group.

Effects of Invention

If a catalyst of the present invention and an electrochemical treatment are employed, carbon monoxide (CO) or formic acid can be efficiently produced from $CO_2$ by simple means even if the $CO_2$ is at a low concentration. Accordingly, carbon monoxide or formic acid which can be various chemical materials can be efficiently produced from a $CO_2$-containing waste gas of facilities, such as a thermal power station or an ironworks, in which a combustion waste gas of an organic matter including petroleum is generated. Accordingly, carbon monoxide or formic acid which can be a raw material of a useful and energy-storing chemical substance such as hydrocarbon or hydrogen can be produced from a combustion waste gas of a fossil fuel such as petroleum, coal or natural gas, and therefore, contribution can be made to both energy reuse and $CO_2$ emission reduction.

DESCRIPTION OF EMBODIMENT

Figure 1:
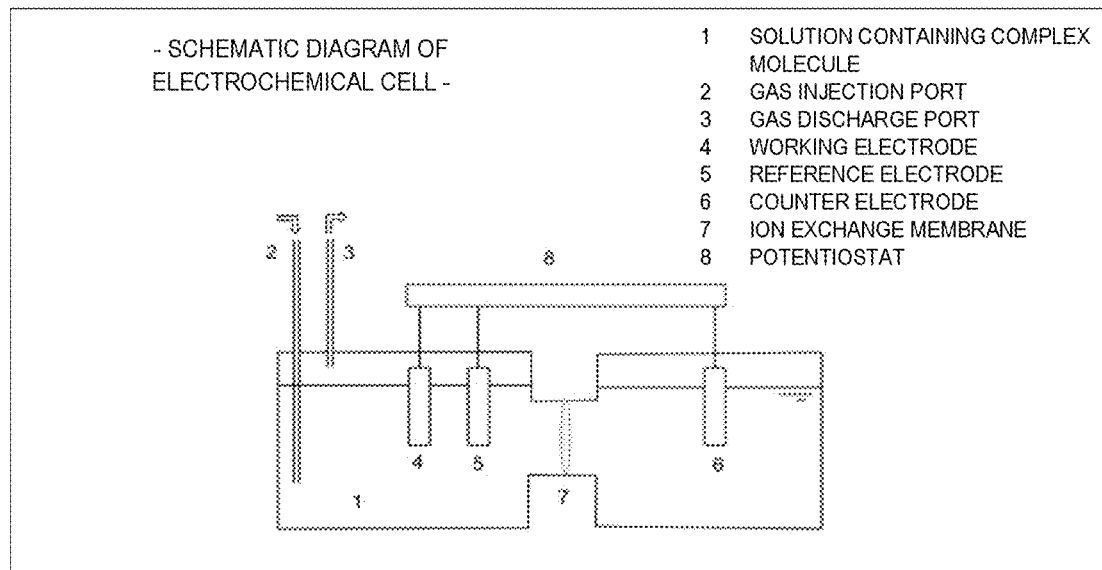
FIG. 1 is a conceptual diagram of a carbon monoxide production system of the present invention.

A catalyst used in electrochemical reduction of CO to CO of the present invention is a metal complex represented by formula (1):

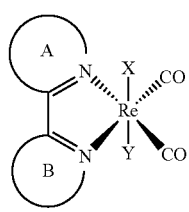

(1)

wherein
X represents $OR^1$, $SR^1$, $NR^2R^3R^4$ or $PX^1X^2X^3$;
Y represents CO, $OR^1$, $SR^1$, $NR^2R^3R^4$ or $PX^1X^2X^3$;
ring A and ring B are identical or different and represent a nitrogen atom-containing heterocycle optionally having a substituent;
$R^1$ represents a hydrocarbon group optionally having a substituent;
one, two or three of $R^2$, $R^3$ and $R^4$ are identical or different and represent a hydrocarbon group optionally having a substituent, the rest representing a hydrogen atom; and
one, two or three of $X^1$, $X^2$ and $X^3$ are identical or different and represent a hydrocarbon group optionally having a substituent or a hydrocarbon oxy group optionally having a substituent, the rest representing a hydrogen atom or a hydroxy group.

On the other hand, a catalyst used in electrochemical reduction of $CO_2$ to formic acid of the present invention is a metal complex represented by formula (2):

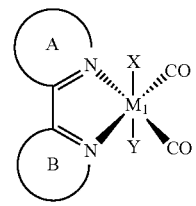

(2)

wherein
$M_1$ represents manganese, ruthenium or iron;
X represents $OR^1$, $SR^1$, $NR^2R^3R^4$ or $PX^1X^2X^3$;
Y represents CO, $OR^1$, $SR^1$, $NR^2R^3R^4$ or $PX^1X^2X^3$;
ring A and ring B are identical or different and represent a nitrogen atom-containing heterocycle optionally having a substituent;
$R^1$ represents a hydrocarbon group optionally having a substituent;
one, two or three of $R^2$, $R^3$ and $R^4$ are identical or different and represent a hydrocarbon group optionally having a substituent, the rest representing a hydrogen atom; and
one, two or three of $X^1$, $X^3$ and $X^3$ are identical or different and represent a hydrocarbon group optionally having a substituent or a hydrocarbon oxy group optionally having a substituent, the rest representing a hydrogen atom or a hydroxy group.

In formula (2), $M_1$ is preferably manganese or ruthenium, and more preferably manganese.

In formulas (1) and (2), X represents $OR^1$, $SR^1$, $NR^2R^3R^4$ or $PX^1X^2X^3$, and Y represents CO, $OR^1$, $SR^1$, $NR^2R^3R^4$ or $PX^1X^2X^3$. X and Y may be identical or different. Here, $R^1$ represents a hydrocarbon group optionally having a substituent. One, two or three of $R^2$, $R^3$ and $R^4$ are identical or different and represent a hydrocarbon group optionally having a substituent, the rest representing a hydrogen atom.

One, two or three of $X^1$, $X^2$ and $X^3$ are identical or different and represent a hydrocarbon group optionally having a substituent or a hydrocarbon oxy group optionally having a substituent, the rest representing a hydrogen atom or a hydroxy group.

The hydrocarbon groups optionally having a substituent represented by $R^1$, $R^2$, $R^3$, $R^4$, $X^1$, $X^2$ and $X^3$ are identical or different, and are preferably any one of an alkyl group, an alkenyl group, a cycloalkyl group, a cycloalkenyl group and an aromatic hydrocarbon group, each of which optionally has one to three substituents selected from the group consisting of a primary, secondary or tertiary amino group, a hydroxy group, an alkoxy group, an aryloxy group, a halogen atom, a nitro group, a cyano group, a formyl group, an alkanoyl group and an arylcarbonyl group.

The alkyl group can be a straight or branched chain alkyl group having 1 to 20 carbon atoms, is preferably a straight or branched chain alkyl group having 1 to 12 carbon atoms, and is more preferably a straight or branched chain alkyl group having 1 to 6 carbon atoms. Specific examples include a methyl group, an ethyl group, a n-propyl group, an isopropyl group, a n-butyl group, an isobutyl group, a sec-butyl group, a tert-butyl group, a n-pentyl group and a n-hexyl group.

The alkenyl group can be a straight or branched chain alkenyl group having 2 to 20 carbon atoms, is preferably a straight or branched chain alkenyl group having 2 to 12 carbon atoms, and is more preferably a straight or branched chain alkenyl group having 2 to 6 carbon atoms. Specific examples include a vinyl group, a 2-propenyl group, a 1-propenyl group and a 1-butenyl group.

The cycloalkyl group can be a $C_3$-$C_8$ cycloalkyl group, and specific examples include a cyclopropyl group, a cyclobutyl group, a cyclopentyl group and a cyclohexyl group. The cycloalkenyl group can be a $C_3$-$C_8$ cycloalkenyl group, and specific examples include a cyclobutenyl group, a cyclopentenyl group and a cyclohexenyl group.

The aromatic hydrocarbon group can be a $C_6$-$C_{14}$ aromatic hydrocarbon group, and specific examples include a phenyl group, a naphthyl group and a phenanthrenyl group.

The hydrocarbon oxy groups optionally having a substituent represented by $X^1$, $X^2$ and $X^3$ are identical or different, and can be any one of an alkoxy group, an alkenyloxy group, a cycloalkyloxy group, a cycloalkenyloxy group and an aromatic hydrocarbon oxy group, each of which optionally has one to three substituents selected from the group consisting of a primary, secondary or tertiary amino group, a hydroxy group, an alkoxy group, an aryloxy group, a halogen atom, a nitro group, a cyano group, a formyl group, an alkanoyl group, and an arylcarbonyl group.

The alkoxy group can be a straight or branched chain alkoxy group having 1 to 20 carbon atoms, is preferably a straight or branched chain alkoxy group having 1 to 12 carbon atoms, and is more preferably a straight or branched chain alkoxy group having 1 to 6 carbon atoms. Specific examples include a methoxy group, an ethoxy group, a n-propyloxy group, an isopropyloxy group, a n-butyloxy group, an isobutyloxy group, a sec-butyloxy group, a tert-butyloxy group, a n-pentyloxy group, and a n-hexyloxy group.

The alkenyloxy group can be a straight or branched chain alkenyloxy group having 2 to 20 carbon atoms, is preferably a straight or branched chain alkenyloxy group having 2 to 12 carbon atoms, and is more preferably a straight or branched chain alkenyloxy group having 2 to 6 carbon atoms. Specific examples include a vinyloxy group, a 2-propenyloxy group, a 1-propenyloxy group, a 1-butenyloxy group, and the like.

The cycloalkyloxy group can be a $C_3$-$C_8$ cycloalkyloxy group, and specific examples include a cyclopropyloxy group, a cyclobutyloxy group, a cyclopentyloxy group and a cyclohexyloxy group. The cycloalkenyloxy group can be a $C_3$-$C_8$ cycloalkenyloxy group, and specific examples include a cyclobutenyloxy group, a cyclopentenyloxy group, a cylohexenyloxy group, and the like.

The aryloxy group can be a $C_6$-$C_{14}$ aryloxy group, and specific examples include a phenyloxy group, a naphthyloxy group, a phenanthrenyloxy group, and the like.

As the group which can be substituted for such a hydrocarbon group or hydrocarbon oxy group, one to three groups selected from the group consisting of an amino group, a $C_{1-6}$ alkylamino group, a di($C_{1-6}$ alkyl)amino group, a di(hydroxy $C_{1-6}$ alkyl)amino group, a hydroxy $C_{1-6}$ alkylamio group, a hydroxy group, a $C_{1-6}$ alkoxy group, a $C_{1-14}$ aryloxy group, a halogen atom, a nitro group, a cyano group, a formyl group, a $C_{1-6}$ alkanoyl group and a $C_{6-14}$ arylcarbonyl group are more preferred. Besides, one to three groups selected from the group consisting of an amino group, a $C_{1-6}$ alkylamino group, a di($C_{1-6}$ alkyl)amino group, a hydroxy $C_{1-6}$ alkylamino group, a di(hydroxy $C_{1-6}$ alkyl)amino group, a hydroxy group, a $C_{1-6}$ alkoxy group, a $C_{1-14}$ aryloxy group, and a halogen atom are further preferred.

One, two or three of $R^2$, $R^3$ and $R^4$ represent any of the above-described hydrocarbon groups, and the rest represents a hydrogen atom. Besides, one, two or three of $X^1$, $X^2$ and $X^3$ represent any of the above-described hydrocarbon groups or hydrocarbon oxy groups, and the rest represents a hydrogen atom or a hydroxy group.

More preferable X is $OR^1$ or $NR^1R^2R^3$.

Further preferable X is —$OC_{2-8}$ alkyl $NHC_{2-8}$ alkyl OH, —$OC_{2-8}$ alkyl $N(C_{1-8}$ alkyl $OH)_2$, —$NH(C_{2-8}$ alkyl OH) or —$N(C_{1-8}$ alkyl $OH)_2$. Further preferable X is —$OC_{2-6}$ alkyl $NHC_{2-6}$ alkyl OH, —$OC_{2-6}$ alkyl $N(C_{2-6}$ alkyl $OH)_2$, —NH ($C_{2-6}$ alkyl OH), or —$N(C_{2-6}$ alkyl $OH)_2$. Still further preferable X is —$OC_2H_4NHC_2H_4OH$, —$C_2H_4N(C_2H_4OH)_2$, —$NH(C_2H_4OH)$ or —$N(C_2H_4OH)_2$. Besides, more preferable Y is CO, $OR^1$ or $NR^2R^3$, and further preferable Y is CO.

As the nitrogen atom-containing heterocycles including ring A and ring B, a heterocycle having a 2,2'-bipyridine structure optionally having a substituent is preferred. As a group which can be substituted in the heterocycle, one to four groups selected from the group consisting of an alkyl group, an alkoxy group, an aryloxy group, a halogen atom and an alkanoyl group are preferred, and one to four groups selected from the group consisting of a $C_{1-6}$ alkyl group, a $C_{1-6}$ alkoxy group, a $C_{6-14}$ aryloxy group, a halogen atom and a $C_{1-6}$ alkanoyl group are more preferred.

As the heterocycle having the 2,2'-bipyridine structure, for example, a heterocycle represented by the following formula (3) or (4) is preferred:

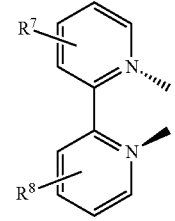

(3)

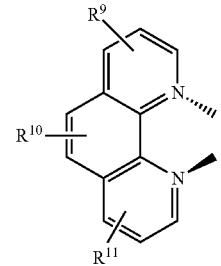

(4)

In the formulas, $R^7$, $R^8$, $R^9$, $R^{10}$ and $R^{11}$ are identical or different, and represent a hydrogen atom, an alkyl group, an alkoxy group, an aryloxy group, a halogen atom or an alkanoyl group.

Among these, the heterocycle of formula (3) is more preferred. More specifically, 2,2'-pyridine, 4,4'-dimethyl-2, 2'-bipyridine, 4,4'-dibromo-2,2'-bipyridine and 4,4'-dimethoxy-2,2'-bipyridine are preferred.

Among metal complexes represented by the aforementioned formula (2), a metal complex represented by the following formula (2a) is novel, and is more preferred:

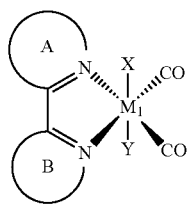

(2a)

In the formula, $M_1$ represents manganese, ruthenium or iron; X represents $O(CH_2)_N NR^5R^6$, $NR^5R^6$ or $PX^1X^2X^3$; Y represents CO, $O(CH_2)$, $NR^5R^6$, $NR^5R^6$ or $PX^1X^2X^3$; ring A and ring B are identical or different and represent a nitrogen atom-containing heterocycle optionally having a substituent; one, two or three of $X^1$, $X^2$ and $X^3$ are identical or different and represent a hydrocarbon group optionally having a substituent or a hydrocarbon oxy group optionally having a substituent, the rest representing a hydrogen atom or a hydroxy group; $R^5$ and $R^6$ are identical or different and represent an alkyl group, a hydroxyalkyl group or a hydrogen atom; and n represents a number of 2 to 8.

As $M^1$, manganese or ruthenium is more preferred, and manganese is further preferred.

As the nitrogen atom-containing heterocycles including ring A and ring B, a heterocycle having a 2,2'-bipyridine structure optionally having a substituent is preferred, a heterocycle of the aforementioned formula (3) or (4) is more preferred, a heterocycle of formula (3) is further preferred, and 2,2'-bipyridine, 4,4'-dimethyl-2,2'-bipyridine, and 4,4'-dibromo-2,2'-bipyridine are particularly preferred.

$R^5$ and $R^6$ in $O(CH_2)_n NR^5R^6$ and $NR^5R^6$ are identical or different, and represent an alkyl group, a hydroxyalkyl group or a hydrogen atom. More specifically, $R^5$ and $R^6$ can be a $C_{1-6}$ alkyl group, a hydroxy $C_{1-6}$ alkyl group or a hydrogen atom, and are preferably a $C_{1-4}$ alkyl group, a hydroxy $C_{1-6}$ alkyl group or a hydrogen atom.

As the hydrocarbon groups optionally having a substituent represented by $X^1$, $X^2$ and $X^3$, any one of an alkyl group, an alkenyl group, a cycloalkyl group, a cycloalkenyl group and an aromatic hydrocarbon group, each of which optionally has one to three substituents selected from the group consisting of a primary, secondary or tertiary amino group, a hydroxy group, an alkoxy group, an aryloxy group, a halogen atom, a nitro group, a cyano group, a formyl group, an alkanoyl group and an arylcarbonyl group, is preferred.

The hydrocarbon oxy groups optionally having a substituent represented by $X^1$, $X^2$ and $X^3$ are identical or different, and can be any one of an alkoxy group, an alkenyloxy group, a cycloalkyloxy group, a cycloalkenyloxy group and an aryloxy group, each of which optionally has one to three substituents selected from the group consisting of a primary, secondary or tertiary amino group, a hydroxy group, an alkoxy group, an aryloxy group, a halogen atom, a nitro group, a cyano group, a formyl group, an alkanoyl group and an arylcarbonyl group.

More preferable X is $O(CH_2)_n NR^5R^5$ or $NR^5R^6$.

Further preferable X is $-OC_{2-8}$ alkyl $NHC_{7-8}$ alkyl OH, $-OC_{2-8}$ alkyl $N(C_{2-8}$ alkyl $OH)_2$, $-NH(C_{2-8}$ alkyl OH) or $-N(C_{2-8}$ alkyl $OH)_2$. Further preferable X is $-OC_{2-6}$ alkyl $NHC_{1-6}$ alkyl OH, $-OC_{2-6}$ alkyl $N(C_{2-6}$ alkyl $OH)_2$, $-NH(C_{2-6}$ alkyl OH) or $-N(C_{2-6}$ alkyl $OH)_2$. Further preferable X is $-OC_2H_4NHC_2H_4OH$, $-OC_2H_4N(C_2H_4OH)_2$, $-NH(C_2H_4OH)$ or $-N(C_2H_4OH)_2$. Besides, more preferable Y is CO, $O(CH_2)_n$ $NR^5R^6$ or $NR^5R^6$, and further preferable Y is CO.

The metal complex represented by formula (1) or (2) can be produced in accordance with, for example, the following reaction formulas:

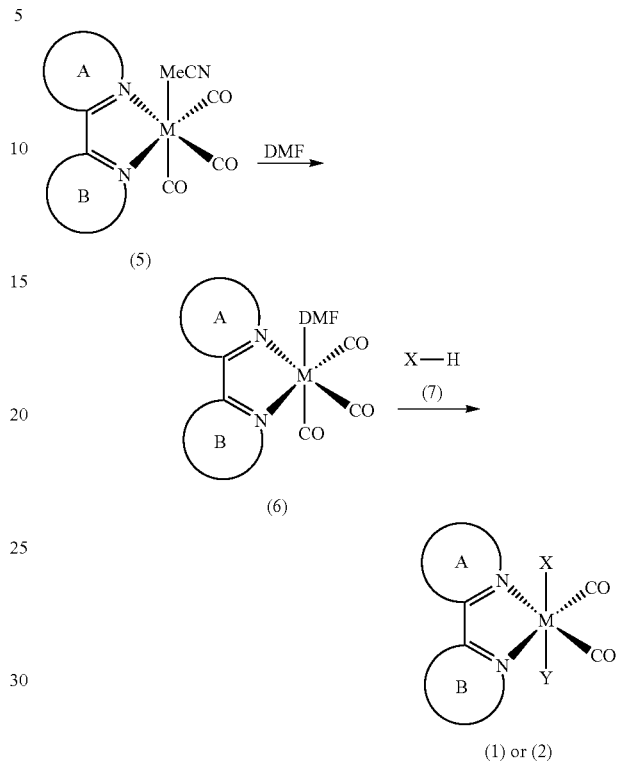

In the formulas, M represents rhenium, manganese, ruthenium or iron, and A, B, X and Y are the same as defined above.

Specifically, an acetonitrile (MeCN)-coordinated metal complex of formula (5) is converted into a solvent-coordinated complex (6) through a reaction with a solvent having comparatively low coordination ability such as dimethylformamide, and the resultant complex is reacted with X—H and/or Y—H (7) in a basic condition, and thus, the metal complex of formula (1) or (2) can be produced. The conversion from the acetonitrile-coordinated complex (5) to the solvent-coordinated complex may be performed by dissolving the complex of formula (5) in the above-described solvent, and allowing the resultant to stand still overnight in a dark place under Ar atmosphere. Next, for producing the complex of formula (1) or (2), the complex of formula (6) is added to X—H (7), and the resultant is allowed to stand still for several hours in a dark place under Ar atmosphere.

A method for producing CO from $CO_2$ by electrochemical reduction of the present invention is characterized by including the following steps (a) and (b):

(a) a step of reacting carbon dioxide with a metal complex represented by formula (1) described above; and (b) a step of applying a voltage to a reaction product of the carbon dioxide and the metal complex represented by formula (1).

Reactions of the steps (a) and (b) are regarded to proceed in accordance with the following reaction formulas:

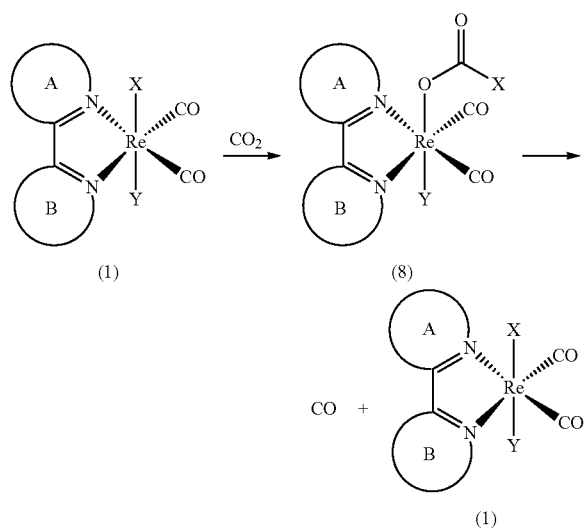

In the formulas, A, B, X and Y are the same as defined above.

Specifically, through the reaction between the metal complex of formula (1) and $CO_2$, a $CO_2$ adduct represented by formula (8) is generated, and when a voltage is applied to this adduct, CO is released. It is noted that the generation of the $CO_2$ adduct of formula (8) can be confirmed based on an IR spectrum, an MS spectrum and an NMR spectrum.

The reaction may be performed in an electrolyte solution, namely, a polar solvent, and from the viewpoint that an oxygen atom produced as a by-product simultaneously with CO released from the $CO_2$ adduct of formula (8) is changed into water through protonation, a protic polar solvent is preferably used. Examples of the protic polar solvent include water, an alcohol-based solvent, an amine-based solvent, a thiol-based solvent and an amino alcohol-based solvent. Among these, a solvent corresponding to X and/or Y of formula (1) is particularly preferably used.

The amount of the metal complex of formula (1) to be used is preferably 0.01 mM to 100 mM in the electrolyte solution, and more preferably 0.05 mM to 10 mM.

The $CO_2$ to be introduced is not necessarily 100% $CO_2$, and the CO generation reaction proceeds even if a gas containing 0.03% to 100% of $CO_2$ is used. The concentration of 0.03% of $CO_2$ gas corresponds to the $CO_2$ concentration in the ambient air. Besides, $CO_2$ of a waste gas containing about 10% of $CO_2$ from a thermal power station or the like can be directly used without concentration.

Besides, the $CO_2$ can be easily introduced by introducing a $CO_2$-containing gas into the electrolyte solution, for example, by bubbling a $CO_2$-containing gas through the electrolyte solution.

Next, for setting an application voltage, it is significant to grasp an application voltage level by precedently performing cyclic voltammetry (CV) measurement. The cyclic voltammetry (CV) measurement is a method in which an electrode potential is linearly swept to measure a response current. In the present invention, the cyclic voltammetry measurement is performed (a) in the absence (blank) or in the presence of the metal complex of the present invention in the electrolyte by introducing (b) Ar gas and (c) a $CO_2$-containing gas. When a current-potential curve is obtained in the condition (c), an application voltage (a reduction potential) can be obtained on the basis of a rising potential of the response current. Incidentally, the voltage may be applied while performing the reaction within an electrochemical cell including a working electrode and a counter electrode. The voltage is preferably 1.0 V to 2.5 V vs. $Ag/AgNO_3$.

Specifically, the steps (a) and (b) are performed within an electrochemical cell including a working electrode and a counter electrode, and the following steps (a1) and (b1) are preferably performed:

(a1) a step of introducing carbon dioxide into a solution containing the metal complex held in the electrochemical cell; and (b1) a step of applying a negative voltage and a positive voltage respectively to the working electrode and the counter electrode of the electrochemical cell.

More specifically, it is preferable to use a system, for example, as illustrated in FIG. 1, for producing carbon monoxide from carbon dioxide through electrochemical reduction, the system including an electrochemical cell part equipped with a solution (1) containing a metal complex, a working electrode (4) and a counter electrode (6); an injection part (an injection port) (2) through which carbon dioxide is injected into the solution containing the metal complex held in the electrochemical cell part (1); a potentiostat (8) including a voltage source capable of applying a positive or negative voltage between the working electrode (4) and the counter electrode (6) of the electrochemical cell part; and a discharge part (a discharge port) (3) through which carbon monoxide generated within the solution containing the metal complex is discharged, so that the carbon monoxide can be generated by applying a positive or negative voltage to a reaction product of the metal complex generated by the solution containing the metal complex and the carbon dioxide.

Figure 2:
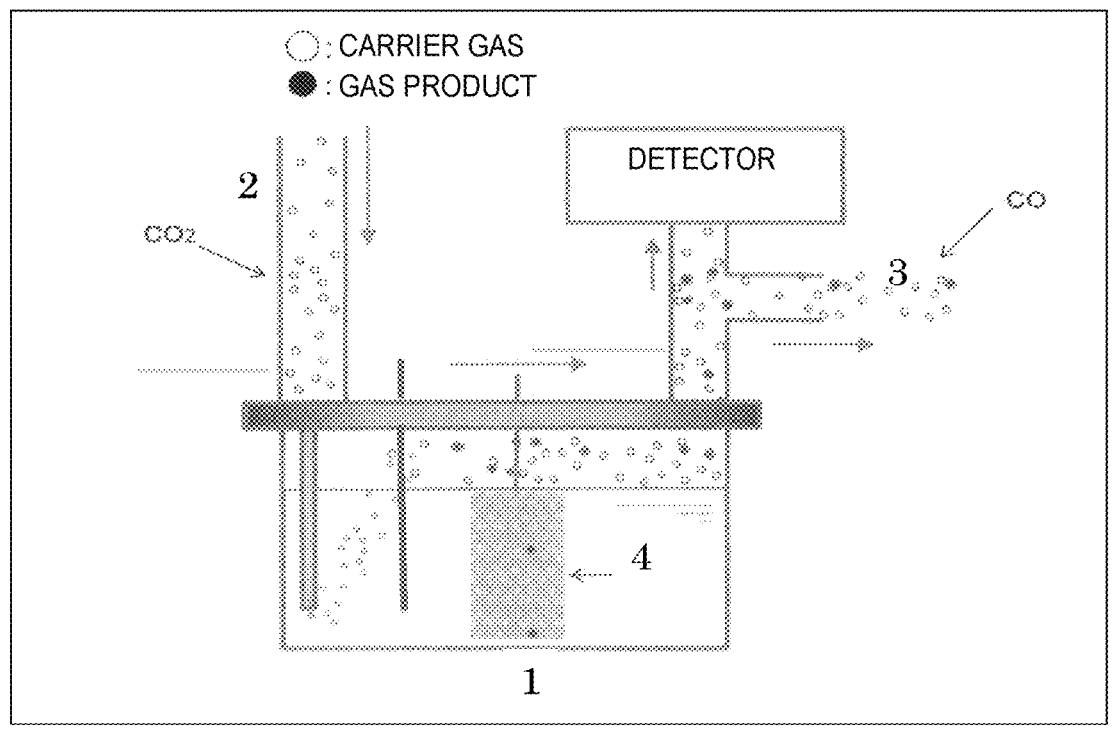
FIG. 2 is a conceptual diagram of an example of a reaction-side cell chamber of the carbon monoxide production system of the present invention. Like reference signs are used in this drawing to refer to like elements of FIG. 1.

FIG. 2 illustrates an apparatus more practical than that illustrated in FIG. 1. The description will now be given on the basis of FIGS. 1 and 2.

In FIGS. 1 and 2, a reference sign (2) denotes a $CO_2$ injection part (injection port), through which $CO_2$ contained in white dots illustrated in FIG. 2 is introduced into a solution containing a metal complex. In FIGS. 1 and 2, a reference sign (1) denotes an electrochemical cell part, and the cell part includes a solution including a working electrode (4), and a reference electrode (5) and a counter electrode (6). Addition of $CO_2$ and a reduction reaction to CO are carried out through the metal complex of the working electrode. Glassy carbon or the like is used as the working electrode. Platinum or the like is used as the counter electrode.

In FIG. 1, a reference sign (8) denotes a potentiostat for applying a positive or negative voltage to the working electrode and the counter electrode of the electrochemical cell part.

In FIG. 2, a reference sign (3) denotes a gas discharge part for discharging CO (illustrated as gray dots) generated within the solution containing the metal complex. This CO discharge part can be provided with any of various CO sensors (of semiconductor type, thermal conductivity type and the like) or a detection part (a detector) detecting generation of carbon monoxide by gas chromatography (Micro-GC).

The system of the present invention can continuously produce CO from a $CO_2$-containing gas having a concentration of about 10% as illustrated in FIGS. 1 and 2, and therefore, can be installed in facilities where $CO_2$ is generated through combustion of organic substances, such as a thermal power station, a cement manufacturing facility and a glass manufacturing facility. Besides, it can be installed in a facility where $Fe_2O_3$ is reduced with CO, such as a blast furnace of an ironworks. In this case, the CO obtained by the method or the system of the present invention can be used as a reducing agent, so as to reproduce CO by using generated $CO_2$ as a raw material. Besides, if CO obtained by the method or the system of the present invention is used as a raw material, a wide range of hydrocarbon-based compounds can be produced.

A method for producing formic acid by electrochemically reducing $CO_2$ of the present invention is characterized by including the following steps (a) and (b):

(a) a step of reacting carbon dioxide with a metal complex represented by formula (2) described above; and (b) a step of applying a voltage to a reaction product of the carbon dioxide and the metal complex represented by formula (2).

Reactions of the steps (a) and (b) are regarded to proceed in accordance with the following reaction formulas:

[Chemical reaction scheme showing formula (2) reacting with $CO_2$ to form formula (9), which releases HCOOH to return to formula (2)]

In the formulas, A, B, $M_1$, X and Y are the same as defined above.

Specifically, through the reaction between the metal complex of formula (2) and $CO_2$, a $CO_2$ adduct represented by formula (9) is generated, and when a voltage is applied to this adduct, formic acid is released. It is noted that the generation of the $CO_2$ adduct of formula (9) can be confirmed based on an IR spectrum and an MS spectrum.

The reaction may be performed in an electrolyte solution, namely, a polar solvent, and from the viewpoint that formic acid is released from the $CO_2$ adduct of formula (9), a protic polar solvent is preferably used. Examples of the protic polar solvent include water, an alcohol-based solvent, an amine-based solvent, a thiol-based solvent and an amino alcohol-based solvent. Among these, a solvent corresponding to X and/or Y of formula (2) is particularly preferably used.

The amount of the metal complex of formula (2) to be used is preferably 0.01 mM to 100 mM in the electrolyte solution, and more preferably 0.05 mM to 10 mM.

The $CO_2$ to be introduced is not necessarily 100% $CO_2$, and the CO generation reaction proceeds even if a gas containing 0.03% to 100% of $CO_2$ is used. The concentration of 0.03% of $CO_2$ gas corresponds to the $CO_2$ concentration in the ambient air. Besides, $CO_2$ of a waste gas containing about 10% of $CO_2$ from a thermal power station or the like can be directly used without concentration.

Besides, the $CO_2$ can be easily introduced by introducing a $CO_2$-containing gas into the electrolyte solution, for example, by bubbling a $CO_2$-containing gas through the electrolyte solution.

Next, for setting an application voltage, it is significant to grasp an application voltage level by precedently performing the cyclic voltammetry (CV) measurement. The cyclic voltammetry (CV) measurement is a method in which an electrode potential is linearly swept to measure a response current. In the present invention, the cyclic voltammetry measurement is performed (a) in the absence (blank) or in the presence of the metal complex of the present invention in the electrolyte by introducing (b) Ar gas and (c) a $CO_2$-containing gas. When a current-potential curve is obtained in the condition (c), an application voltage (a reduction potential) can be obtained on the basis of a rising potential of the response current. Incidentally, the voltage may be applied while performing the reaction within an electrochemical cell including a working electrode and a counter electrode. The voltage is preferably 1.0 V to 2.5 V vs. $Ag/AgNO_3$.

According to the method of the present invention, formic acid can be continuously produced from a $CO_2$-containing gas having a concentration of about 0.03%, and therefore, the method can be employed in facilities where $CO_2$ is generated through combustion of organic substances, such as a thermal power station, a cement manufacturing facility and a glass manufacturing facility.

EXAMPLES

Next, the present invention will be described in more detail with reference to examples.

Synthesis Example 1

$Re(CO)_5Br$

Four (4) mL of bromine was added in a dropwise manner to dichloromethane (8 mL) containing $Re_2(CO)_{10}$ (4.71 g, 7.21 mmol), and the resultant was stirred at room temperature for 10 minutes. A white solid thus separated was filtered off.

Yield: 5.47 g (13.4 mmol), Yield: 93.1%

FT-IR in $CH_2Cl_2$ $\nu(CO)/cm^{-1}$: 2154, 2046, 1988

Synthesis Example 2

$Re(bpy)(CO)_3Br$ (sometimes abbreviated as Re—Br)

A toluene solution (60 mL) containing $Re(CO)_5Br$ (3.00 g, 7.38 mmol) and 2,2'-bipyridine (bpy) (1.27 g, 8.14 mmol) was heated to reflux overnight. A yellow solid thus separated was filtered off and dried under reduced pressure. The resultant was purified by recrystallization using acetonitrile/diethyl ether/hexane.

Yield: 3.63 g (7.18 mmol), Yield: 97.3%

ESI-MS in $CH_2Cl_2$ m/z=468 $[M-PF_6^+]^+$

FT-IR in $CH_2Cl_2$ $\nu(CO)/cm^{-1}$: 2024, 1923, 1901

$^1$H NMR in $CDCl_3$: δ (ppm)=9.09 (d, J=7.0 Hz, 2H, bpy-6,6'), 8.21 (d, J=7.0 Hz, 2H, bpy-3,3'), 8.07 (dd, J=7.0, 7.0 Hz, 2H, bpy-4,4'), 7.55 (dd, J=7.0, 7.0 Hz, 2H, bpy-5,5')

Elemental analysis: Calcd. (%) for $C_{13}H_{10}N_2O_3BrRe$: C, 30.84; H, 1.59; N, 5.53.

Found: C, 30.86; H, 1.46; N, 5.61.

Synthesis Example 3

Re(dmb)(CO)$_3$Br

A toluene solution (60 mL) containing Re(CO)$_5$Br (1.10 g, 2.71 mmol) and 4-4'-dimethyl-2,2'-bipyridine (dmb) (0.55 g, 3.00 mmol) was heated to reflux overnight. A yellow solid thus separated was filtered off and dried under reduced pressure.

Yield: 1.40 g (2.62 mmol), Yield: 96.7%
FT-IR in CH$_2$Cl$_2$ ν(CO)/cm$^{-1}$: 2022, 1920, 1898

Synthesis Example 4

Re{(MeO)$_2$bpy}(CO)$_3$Br

A toluene solution (60 mL) containing Re(CO)$_3$Br (499 mg, 1.23 mmol) and 4,4'-dimethoxy-2,2'-bipyridine (1MeO)$_2$bpy (321 mg, 1.483 mmol) was heated to reflux overnight. A yellow solid thus separated was filtered off and dried under reduced pressure.

Yield: 652 mg (1.15 mmol), Yield: 93.7%
FT-IR in CH$_2$Cl$_2$ ν(CO)/cm$^{-1}$: 2022, 1918, 1895

Synthesis Example 5

Re(Br$_2$bpy)(CO)$_3$Br

A toluene solution (60 mL) containing Re(CO)$_5$Br (503 mg, 1.24 mmol) and 4-4'-dibromo-2,2'-bipyridine (Br$_2$bpy) (464 mg, 1.48 mmol) was heated to reflux overnight. A yellow solid thus separated was filtered off and dried under reduced pressure.

Yield: 803 mg (1.21 mmol), Yield: 97.7%
FT-IR in CH$_2$Cl$_2$ ν(CO)/cm$^{-1}$: 2026, 1928, 1905

Synthesis Example 6

[Re(bpy)(CO)$_3$(MeCN)](PF$_6$) (Sometimes Abbreviated as Re-MeCN)

Acetonitrile (60 mL) containing Re(bpy)(CO)$_3$Br (596 mg, 1.18 mmol) and AgPF$_6$ (327 mg, 1.29 mmol) was heated to reflux overnight. AgBr thus separated was removed over a Celite layer, and the solvent was distilled off under reduced pressure. To the resultant, saturated NH$_4$PF$_6$ in acetonitrile/water (1:1 v/v) was added, and the acetonitrile was slowly distilled off under reduced pressure to obtain a pale yellow solid. This solid was recrystallized from acetonitrile/diethyl ether/hexane, and a yellow solid thus obtained was dried under reduced pressure.

Yield: 363 mg, (5.92×10$^{-1}$ mmol), Yield: 50.3%
ESI-MS in MeCN m/z=468 [M-PF$_6^-$]$^+$
FT-IR in MeCN ν(CO)/cm$^{-1}$: 2041, 1938
$^1$H-NMR in CD3CN (298 MHz): δ (ppm)=9.02 (dd, J=5.6, 1.5 Hz, 2H, bpy-6,6'), 8.47 (dd, J=8.2, 1.1 Hz, 2H, bpy-3,3'), 8.28 (ddd, J=8.2, 8.2, 1.5 Hz, 2H, bpy-4,4'), 7.71 (ddd, J=8.2, 5.6, 1.1 Hz, 2H, bpy-5,5'), 2.03 (s, 3H, CH$_3$CN)
Elemental analysis: Calcd. (%) for C$_{15}$H$_{13}$N$_3$O$_3$RePF$_6$: C, 29.40; H, 1.81; N, 6.86.
Found: C, 29.35; H, 1.65; N, 6.91.

Synthesis Example 7

[Re(dmb)(CO)$_3$(MeCN)](PF$_6$) (sometimes abbreviated as (Re(Me)MeCN)

An acetonitrile solution (60 mL) containing Re(dmb)(CO)$_3$Br (500 mg, 9.34×10$^{-1}$ mmol) and AgPF$_6$ (303 mg, 1.19 mmol) was heated to reflux overnight. AgBr thus separated was removed over a Celite layer, and the solvent was distilled off under reduced pressure. To the resultant, saturated NH$_4$PF$_6$ in acetonitrile/water (1:1 v/v) was added, and the acetonitrile was slowly distilled off under reduced pressure to obtain a pale yellow solid. This solid was recrystallized from acetonitrile/diethyl ether/hexane, and a pale yellow solid thus obtained was dried under reduced pressure.

Yield: 478.6 mg, (7.47×10$^{-1}$ mmol), Yield: 79.9%
ESI-MS in MeCN m/z=496 [M-PF$_6^-$]$^+$
FT-IR in MeCN ν(CO)/cm$^{-1}$: 2039, 1935
$^1$H-NMR in CD3CN (298 MHz): δ (ppm)=8.82 (d, J=5.5 Hz, 2H, bpy-6,6'), 8.32 (s, 2H, bpy-3,3'), 7.52 (d, J=5.5 Hz, 2H, bpy-5,5'), 2.58 (s, 6H, bpy-CH$_3$), 2.04 (s, 3H, CH$_3$—CN)
Elemental analysis: Calcd. (%) for C$_{17}$H$_{15}$N$_3$O$_3$RePF$_6$: C, 31.88; H, 2.36; N, 6.56.
Found: C, 31.85; H, 2.19; N, 6.59

Synthesis Example 8

[Re{(MeO)$_2$bpy}(CO)$_3$(MeCN)](PF$_6$) (sometimes abbreviated as Re(MeO)MeCN)

An acetonitrile solution (60 mL) containing Re{(MeO)$_2$bpy}(CO)$_3$Br (601 mg, 1.06 mmol) and AgPF$_6$ (290 mg, 1.15 mmol) was heated to reflux overnight. AgBr thus separated was removed over a Celite layer, and the solvent was distilled off under reduced pressure. To the resultant, saturated NH$_4$PF$_6$ in acetonitrile/water (1:1 v/v) was added, and the acetonitrile was slowly distilled off under reduced pressure to obtain a pale yellow solid. This solid was recrystallized from acetonitrile/diethyl ether/hexane, and a pale yellow solid thus obtained was dried under reduced pressure.

Yield: 443 mg (6.59×10$^{-1}$ mmol), Yield: 62.1%
ESI-MS in MeCN m/z=528 [M-PF$_6^-$]$^+$
FT-IR in MeCN ν(CO)/cm$^{-1}$: 2038, 1932
$^1$H-NMR in CD$_3$CN (298 MHz): δ (ppm)=8.76 (d, J=6.6 Hz, 2H, bpy-6,6'), 7.92 (d, 2.7 Hz, 2H, bpy-3,3'), 7.19 (dd, J=2.7, 6.6 Hz, 2H, bpy-5,5'), 4.03 (s, 6H, CH$_3$O), 2.05 (s, 3H, CH$_3$—CN)
Elemental analysis: Calcd. (%) for C$_{17}$H$_{15}$N$_3$O$_5$RePF$_6$: C, 30.36; H, 2.25; N, 6.25.
Found: C, 30.85; H, 2.24; N, 6.43.

Synthesis Example 9

[Re(Br$_2$bpy)(CO)$_3$(MeCN)](PF$_6$) (sometimes abbreviated as Re(Br)MeCN)

An acetonitrile solution (60 mL) containing Re(Br$_2$bpy)(CO)$_3$Br (600 mg, 9.04×10$^{-1}$ mmol) and AgPF$_6$ (242.4 mg, 9.59×10$^{-1}$ mmol) was heated to reflux overnight. AgBr thus separated was removed over a Celite layer, and the solvent was distilled off under reduced pressure. To the resultant, saturated NH$_4$PF$_6$ in acetonitrile/water (1:1 v/v) was added, and the acetonitrile was slowly distilled off under reduced pressure to obtain a pale yellow solid. This solid was recrystallized from acetonitrile/diethyl ether/hexane, and a reddish brown solid thus obtained was dried under reduced pressure.

Yield: 435 mg (5.65×10$^{-1}$ mmol), Yield: 62.5%
ESI-MS in MeCN m/z=626 [M-PF$_6^-$]$^+$
FT-IR in MeCN η(CO)/cm$^{-1}$: 2042, 1941
$^1$H-NMR in CD$_3$CN (298 MHz): δ (ppm)=8.81 (d, J=6.0 Hz, 2H, bpy-6,6'), 8.72 (d, 2.0 Hz, 2H, bpy-3,3'), 7.92 (dd, J=2.0, 6.0 Hz, 2H, bpy-5,5'), 2.06 (s, 3H, CH$_3$—CN)
Elemental analysis: Calcd. (%) for C$_{15}$H$_9$N$_3$OBr$_2$RePF$_6$: C, 23.39; H, 1.18; N, 5.46.
Found: C, 23.56; H, 1.10; N, 5.62

Synthesis Example 10

Re(bpy)(CO)$_3$(OCOH) (Sometimes Abbreviated as Re—OCOH)

An ethanol/water mixed solution (1:1 v/v, 50 mL) containing Re(bpy)(CO)$_3$Br (301 mg, 5.95×10$^{-1}$ mmol) and an excessive amount of sodium formate (4.05 g, 59.6 mmol) was heated to reflux overnight. The ethanol was slowly distilled off under reduced pressure. Dichloromethane was added thereto, and the resultant was extracted with water three times. After distilling off the solvent of the thus obtained organic layer under reduced pressure, the resultant was recrystallized from acetone/diethyl ether/hexane, and a yellow solid thus obtained was dried under reduced pressure.

Yield: 70.4 mg (1.49×10$^{-1}$ mmol), Yield: 25.1%

ESI-MS in MeCN m/z=626 [M-PF$_6$$^+$]$^+$

FT-IR in CH$_2$Cl$_2$ ν(CO)/cm$^{-1}$: 2022, 1918, 1896

$^1$H-NMR in CD3CN (298 MHz): δ (ppm)=9.02 (dd, 2H, J=5.6, 1.6 Hz, bpy-6,6'), 8.40 (dd, 2H, J=8.3, 1.1 Hz, bpy-3,3'), 8.20 (ddd, 2H, J=8.3, 8.3, 1.6 Hz, bpy-4,4'), 7.61 (ddd, 2H, J=8.3, 5.6, 1.1 Hz, bpy-5,5'), 7.81 (s, 1H, HCOO)

Elemental analysis: Calcd. (%) for C$_{14}$H$_9$N$_2$O$_5$Re: C, 35.67; H, 1.92; N, 5.94.

Found: C, 35.63; H, 1.82; N, 6.01

Synthesis Example 11

Re(bpy)(CO)$_3$(OTf)

A tetrahydrofuran solution (60 mL) containing Re(bpy)(CO) Br (1.00 g, 1.97 mmol) and AgOTf (553 mg, 2.15 mmol) was heated to reflux overnight. AgBr thus separated was removed over a Celite layer, and the solvent was distilled off under reduced pressure. The thus separated solid was recrystallized from dichloromethane/dimethyl ether/hexane, and a yellowish brown solid thus obtained was dried under reduced pressure.

Yield: 902 mg (1.56 mmol), Yield: 79.0%

FT-IR ν$_{CO}$ [cm$^{-1}$] in CH$_2$Cl$_2$: 2036, 1935, 1915

Synthesis Example 12

[Re{4,4'-(MeO)$_2$bpy}(CO)$_3${P(OC$_2$H$_5$)$_3$}](PF$_6$)

A tetrahydrofuran solution containing Re[4,4'-(MeO)$_2$bpy(CO)$_3$MeCN] (501 mg, 7.44×10$^{-1}$ mmol) and P(OC$_2$H$_5$)$_3$ (ca. 1 mL, 6 mmol) was heated to reflux in a dark place overnight. While blocking light, the solvent and an unreacted portion of P(OC$_2$H$_5$)$_3$ were distilled off under reduced pressure by using an oil sealed rotary pump. The thus obtained solid was recrystallized from dichloromethane/diethyl ether, and the resultant was separated and purified by flash column chromatography (elution solution: dichloromethane:methanol=100:0 to 100:3 v/v). The third fraction thus obtained was further recrystallized from dichloromethane/dimethyl ethanol, and a pale yellow solid thus obtained was dried under reduced pressure. Yield:

413 mg (5.18×10$^{-1}$ mmol), Yield: 69.6%

ESI-MS in MeCN m/z=653 [M-PF$_6$$^-$]$^+$

FT-IR in CH$_2$Cl$_2$ ν(CO)/cm$^{-1}$: 2044, 1958, 1925

$^1$H-NMR in CD$_3$CN (298 MHz): δ (ppm)=8.59 (d, J=6.4 Hz, 2H, bpy-6,6'), 7.94 (d, J=2.6 Hz, 2H, bpy-3,3'), 7.09 (dd, J=2.6, 6.4 Hz, 2H, bpy-5,5'), 4.16 (s, 6H, CH$_3$O), 3.82 (quin, J=7.1, 7.1, 7.1, 7.1 Hz, 6H, OCH$_2$CH$_3$), 1.09 (t, J=7.1, 7.1 Hz, 9H, OCH$_2$CH$_3$)

Elemental analysis: Calcd. (%) for C$_{21}$H$_{27}$N$_2$O$_9$F$_6$P$_2$Re: C, 31.62; H, 3.41; N, 3.51.

Found: C, 31.67; H, 3.25; N, 3.57.

Synthesis Example 13

Re(bpy)(CO)$_3$(OH)

An acetone/water mixed solution (4:3 v/v, 70 mL) containing Re(bpy)(CO)$_3$(OTf) (303 mg, 5.21×10$^{-1}$ mmol) and potassium hydroxide (1.35 g, 24.1×10 mmol) was heated to reflux overnight. The acetone was slowly distilled off under reduced pressure, and a yellow solid thus separated was filtered off and dried under reduced pressure.

Yield: 120 mg (2.71×10$^{-1}$ mmol), Yield: 51.5%

Synthesis Example 14

Re(bpy)(CO)$_3$(OCO$_2$H)

A CO$_2$ gas was allowed to pass through an acetone solution containing Re(bpy)(CO)$_3$(OH) (52.0 mg, 1.17×10$^{-1}$ mmol) for 20 minutes. A yellow solid thus separated was filtered off and dried under reduced pressure.

Yield: 51.5 mg (1.06×10$^{-1}$ mmol), Yield: 90.1%

FT-IR in KBr ν(CO)/cm$^{-1}$: 2022, 1895, 1616, 1602

Synthesis Example 15

[Re(bpy)(CO)$_3$(DMF)](PF$_6$)

[Re(bpy)(CO)$_3$(MeCN)](PF$_6$) (56.3 mg, 92.0 µmol) was dissolved in DMF-d$_7$, and the resultant was allowed to stand still in a dark place under Ar atmosphere for 12 hours to completely replace a MeCN ligand with DMF.

$^1$H NMR in DMF-d$_7$ (500 MHz): δ (ppm)=9.27 (ddd, 2H, J=0.5, 1.0, 5.5 Hz, bpy-6,6'), 8.95 (d, 2H, J=8.0 Hz, bpy-3,3'), 8.54 (ddd, 2H, J=1.0, 8.0, 8.0 Hz, bpy-4,4'), 7.97 (ddd, 2H, J=1.0, 5.5, 8.0 Hz, bpy-5,5')

$^{13}$C NMR in DMF-d, (126 MHz): δ (ppm)=196.9, 193.2, 156.5, 154.9, 142.0, 128.9, 125.2

FT-IR in DMF ν(CO)/cm$^{-1}$: 2029, 1922, 1913

Synthesis Example 16

Re(bpy)(CO)$_3${O—CO—OCH$_2$CH$_2$N(CH$_2$CH$_2$OH)$_2$}

To a DMF solution (2 mL) containing [Re(bpy)(CO) 3 (DMF)]+, triethanolamine (TEOA, 200 µL) was added. The resultant was allowed to stand still for 12 hours to partially replace a DMF ligand with TEOA, and thus, the resultant was changed to an equilibrium mixture of [Re(bpy)(CO)$_3$(DMF)]$^+$ and Re(bpy)(CO)$_3$(TEOA).

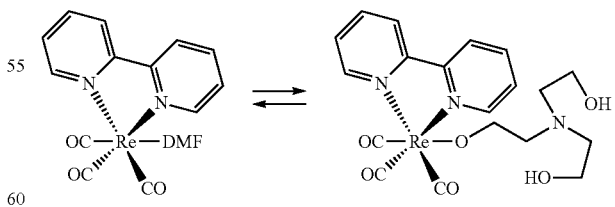

Through the resultant solution, CO$_2$ was allowed to pass for 30 minutes. At this point, Re(bpy)(CO)$_3$OCO$_2$H was precipitated and hence was filtered off, and the resultant filtrate was used as a sample solution for an NMR spectrum.

$^1$H NMR in DMF-d$_7$-TEOA (10:1 v/v) (500 MHz): δ (ppm)=9.19 (ddd, 2H, J=0.5, 1.0, 5.5 Hz, bpy-6,6'), 8.82 (d, 2H, J=8.0 Hz, bpy-3,3'), 8.42 (ddd, 2H, J=1.0, 8.0, 8.0 Hz, bpy-4,4'), 7.87 (ddd, 2H, J=1.0, 5.5, 8.0 Hz, bpy-5,5')

$^{13}$C NMR in DMF-d$_7$-TEOA (10:1 v/v) (126 MHz) δ (ppm)=198.4, 194.4, 158.4 (C=O), 156.0, 153.8, 140.9, 128.0, 124.4

FT-IR in DMF-TEOA (5:1 v/v) ν(CO)/cm$^{-1}$: 2020, 1915, 1892

ESI-MS in MeCN m/z=620 [M+H$^+$—PF$_6^-$]$^+$, 642 [M+Na$^+$—PF-]$^+$

Synthesis Example 17

Mn(bpy)(CO)$_3$Br

A diethyl ether solution (400 mL) containing 2,2'-bipyridine (bpy) (0.57 g, 3.65 mmol) and Mn(CO)$_3$Br (1.0 g, 3.65 mmol) was heated to reflux for 3 hours. An orange powder thus separated was filtered off, washed with diethyl ether, and dried under reduced pressure.

Yield: 1.26 g (92.6%)

$^1$H NMR (400 MHz, aceton-d$_6$, ppm) δ=9.30 (d, 2H, J=4.8 Hz; 2H; H6,6'), 8.58 (d, 2H, J=8.2 Hz, H3,3'), 8.23 (td, 2H, J=5.9 Hz), 7.75 (t, J=5.9 Hz, 2H; H5,5').

FT-IR (CH$_2$Cl$_2$): ν(CO)/cm$^{-1}$, 2028, 1938, 1922.

Synthesis Example 18

[Mn(bpy)(CO)$_3$CH$_3$CN]PF$_6$

An acetonitrile solution (350 mL) containing AgPF$_6$ (0.69 g, 3.65 mmol) and Mn(bpy)(CO)$_3$Br (1.00 g, 2.71 mmol) was heated to 40° C. for 1 hour. The thus obtained mixture was filtered through Celite. The resultant filtrate was evaporated to dryness, and the thus obtained solid was washed with diethyl ether and dried under reduced pressure.

Yield: 1.23 g (96.0%)

$^1$H NMR (400 MHz, CD$_3$Cl$_3$, ppm) δ=9.04 (d, 2H, J=3.6 Hz; 2H; H6,6'), 8.41 (d, 2H, J=7.6 Hz, H3,3'), 8.22 (td, 2H, J=5.9 Hz, H4,4'), 7.66 (t, 2H, J=5.9 Hz, H5,5'), 2.10 (s, 3H, CH$_3$)

FT-IR (CH$_3$CN): ν(CO)/cm$^{-1}$, 2028, 1938, 1923.

Elemental Anal. Calcd (%) for C$_{13}$H$_8$BrMnN$_2$O$_3$: C, 37.44: H, 2.30; N, 8.73.

Found: C, 37.56: H, 2.21; N, 8.83.

Synthesis Example 19

Mn(MeObpy)(CO)$_3$Br

Mn(MeOpby)(CO)$_3$Br was obtained in the same manner as the synthesis of Mn(bpy)(CO)$_3$Br of Synthesis Example 18.

Yield: 96.3%

$^1$H NMR (400 MHz, aceton-d$_6$, ppm) δ=9.02 (d, 2H, J=6.4 Hz; H6,6'), 8.13 (d, 2H, J=2.0 Hz, H3,3'), 7.30 (dd, 2H, J=6.4, 2.0 Hz, H5,5'), 4.12 (s, 6H, OCH$_3$)

FT-IR (CH$_2$Cl$_2$): ν(CO)/cm$^{-1}$ 2026, 1930, 1918.

Synthesis Example 20

[Mn(MeObpy)(CO)$_3$CH$_3$CN]PF$_6$

[Mn(MeObpy)(CO)$_3$CH$_3$CN]PF$_6$ was obtained in the same manner as the synthesis of [Mn(bpy)(CO)$_3$CH$_3$CN]PF$_6$ of Synthesis Example 18

Yield: 75.1%

$^1$H NMR (400 MHz, CD$_3$Cl$_3$, ppm) δ=8.72 (d, 2H, J=6.4 Hz; 2H; H6,6'), 7.81 (d, 2H, J=2.6Ha, H3,3'), 7.82 (td, 2H, J=2.6, 6.4 Hz, H4,4'), 4.11 (s, 6H, OCH$_3$), 2.16 (s, 3H, NCCH$_3$)

FT-IR (CH$_3$CN): ν(CO)/cm$^{-1}$, 2047, 1953.

Synthesis Example 21

Mn(Brbpy)(CO)$_3$Br

Mn(Brbpy)(CO)$_3$Br was obtained in the same manner as the synthesis of Mn(bpy)(CO)$_3$Br of Synthesis Example 17.

Yield: 0.64 g (94.5%)

$^1$H NMR (400 MHz, aceton-d$_6$, ppm) δ=9.17 (d, 2H, J=6.0 Hz, 2H, H6,6'), 8.94 (d, 2H, J=1.8 Hz, H3,3'), 8.01 (dd, 2H, J=5.6, 1.8 Hz, H5,5')

FT-IR (CH$_7$Cl$_7$): ν(CO)/cm$^{-1}$, 2030, 1938.

Synthesis Example 22

[Mn(Brbpy)(CO)$_3$CH$_3$CN]PF$_6$

[Mn(Brbpy)(CO)$_3$CH$_3$CN]PF$_6$ was obtained in the same manner as the synthesis of [Mn(bpy)(CO)$_3$CH$_3$CN]PF$_6$ of Synthesis Example 18.

Yield: 1.23 g (96.6%)

$^1$H NMR (400 MHz, CDCl$_3$, ppm) δ=8.83 (d, 2H, J=5.8 Hz; 2H; H6,6'), 8.42 (d, 2H, J=2.2 Hz, H3,3'), 7.82 (td, 2H, J=2.2, 5.8 Hz, H4,4'), 2.16 (s, 3H, CH$_3$, H)

FT-IR (CH$_3$CN): ν(CO)/cm$^{-1}$, 2051, 1963.

Elemental Anal. Calcd (%) for C$_{15}$H$_9$Br$_2$MnN$_3$O3: C, 28.20; H, 1.42; N, 6.58.

Found: C, 28.50; H, 1.28; N, 6.69.

Synthesis Example 23 (CO$_2$ Addition Reaction to Metal Complex of Formula (1))

(1) Generation of Re—CO$_2$-TEOA in DMF-TEOA Mixed Solution

CO$_2$ was allowed to pass through a solution containing a rhenium complex to attempt to observe a rhenium complex to which CO$_2$ had been added.

Figure 3:
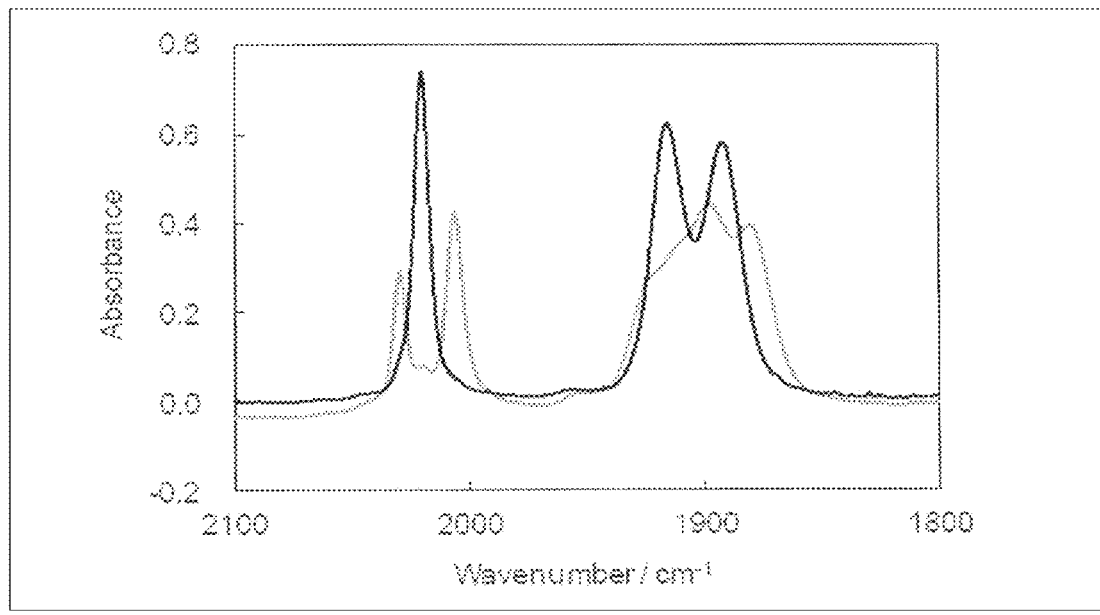
FIG. 3 illustrates IR spectrum change (solvent: DMF-TEOA (5:1 v/v)) obtained by allowing $CO_2$ to pass for 30 minutes through a solution 4 hours after adding TEOA. Spectrum obtained before the passage: gray line, spectrum obtained after the passage: black line
Figure 4:
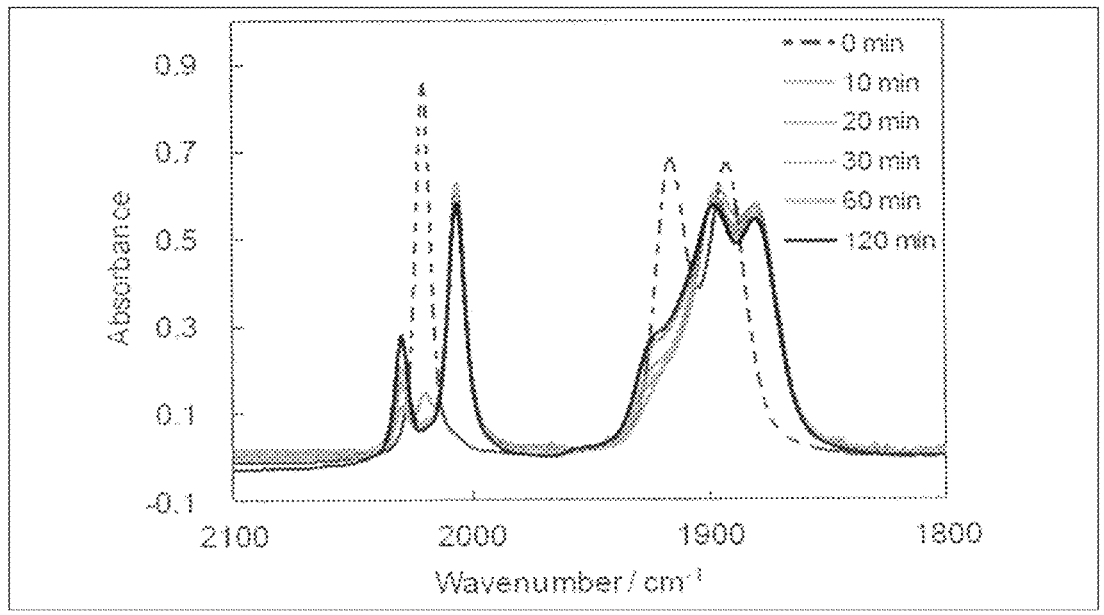
FIG. 4 illustrates IR spectrum change (solvent: DMF-TEOA (5:1 v/v)) obtained by allowing Ar to pass through the solution after allowing the $CO_2$ to pass (after 0 to 120 minutes).

Re-MeCN was dissolved in DMF to a concentration of 5.30 mM, and the resultant was allowed to stand still in a dark place under Ar atmosphere. Thereafter, TEOA was added thereto, and the resultant was allowed to stand still again in a dark place under Ar atmosphere. Then, CO$_2$ was allowed to pass through the thus obtained DMF-TEOA mixed solution for 30 minutes. IR spectrum change of the resultant solution is illustrated in FIG. 3. Besides, change in color of the solution was observed. Furthermore, Ar was allowed to pass for 2 hours through the solution through which CO$_2$ had passed, so as to remove dissolved CO$_2$ from the solution. IR spectrum change thus caused is illustrated in FIG. 4.

When CO$_2$ was allowed to pass through this equilibrium mixture, all peaks precedently observed disappeared, and new peaks were observed at 2020 cm$^{-1}$, 1915 cm$^{-1}$ and 1892 cm$^{-1}$ (FIG. 3). It can be determined based on the shapes of these IR peaks that a newly produced complex retains a tricarbonyl structure. Besides, when CO$_2$ was allowed to pass through, the color of the solution was changed from reddish brown to yellow, which suggests that some sort of reaction was caused between Re-DMF or Re-TEOA and CO$_2$. Even if CO$_2$ was allowed to pass through a DMF solution containing Re-DMF, the IR spectrum was not changed. Accordingly, it is presumed that the reaction is caused between Re-TEQA and $CO_2$. Besides, the peak of the newly produced complex (Re—$CO_2$-TEOA) is positioned on a lower frequency side of the peak of Re-DMF but on a higher frequency side of the peak of Re-TEOA. This relationship in the wavelength reveals that the electron-donating property of a ligand of Re—$CO_2$-TEOA is stronger than that of a DMF ligand but weaker than that of a TEOA ligand.

When Ar was allowed to pass through, the peaks of Re—$CO_2$-TEOA were largely reduced, and mainly the peaks of Re-TEOA were recovered. After 2 hours, the peaks of Re-$CO_2$-TEOA completely disappeared (FIG. 4), and a concentration ratio between Re-DMF and Re-TEOA became substantially the same as that in the equilibrium state obtained before allowing $CO_2$ to pass therethrough. Accordingly, it was found that the generation reaction of Re—$CO_2$-TEOA is reversible and that the equilibrium depends on the $CO_2$ concentration in the solution.

(2) Determination of Structure of Re—$CO_2$-TEOA

An attempt was made to specify the structure of Re—$CO_2$-TEOA from the MS spectrum and the NMR spectrum thereof.

Figure 5:
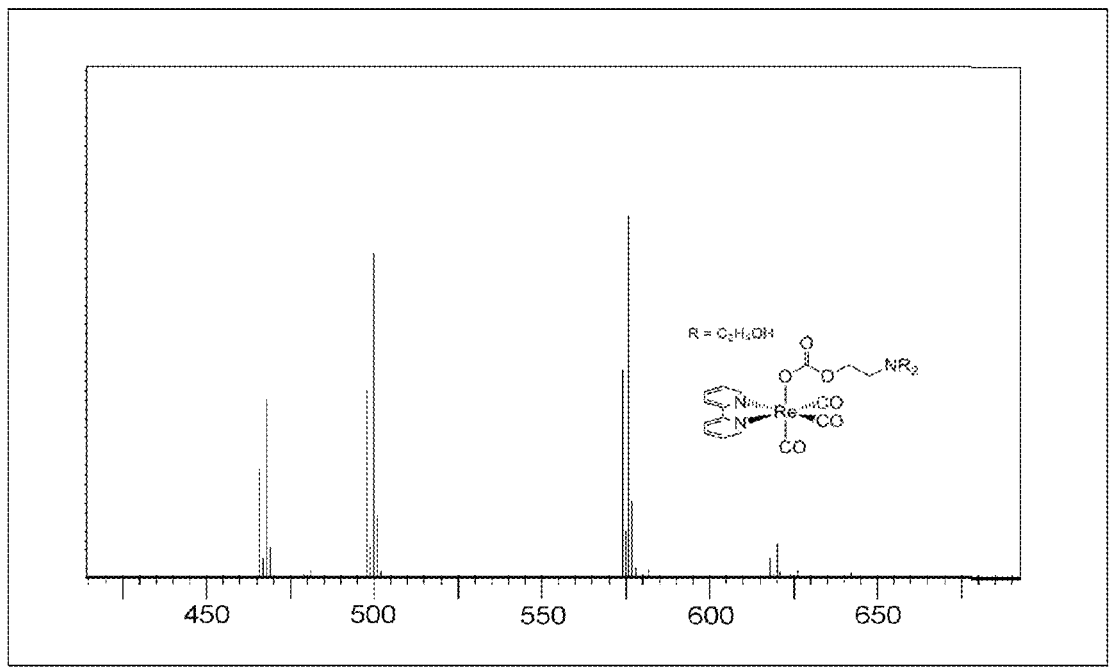
FIG. 5 illustrates an ESI-MS spectrum (solvent: MeCN) of a DMF-TEOA mixed solution (5:1 v/v) containing Re—$CO_2$-TEOA.

FIG. 5 illustrates an ESI-MS spectrum of a DMF-TEOA mixed solution (5:1 v/v) containing Re—$CO_2$-TEOA. Peaks were mainly observed at not only Re-MeCN (m/z=468), Re-DMF (m/z=500) and Re-TEOA (m/z=576) but also m/z=620.

The peak at m/z=620 corresponds to a monovalent complex (m/z=619.62) resulting from addition of $CO_2$ (exact mass=44.01) and TEOA (exact mass=149.19) to Re(bpy)(CO)$_3$ (exact mass=426.42).

It was concluded, on the basis of $^1$H-NMR and $^{13}$C-NMR, that Re(bpy)(CO)$_3${O—CO—OCH$_2$CH$_2$N(CH$_2$CH$_2$OH)$_2$} represented by the following formula had been generated:

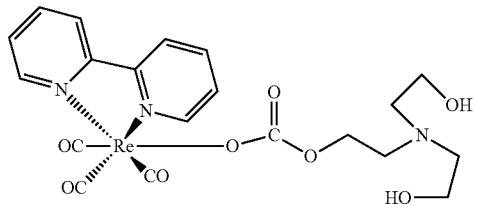

(3) Uptake of $CO_2$ from Air by Re-TEOA

With general air allowed to pass through instead of 100% $CO_2$ gas, it was checked whether or not $CO_2$ in the ambient air was taken in by Re-TEOA. Besides, with an electron-withdrawing or electron-donating substituent introduced into the 4,4'-position of the bpy ligand, the relationship between the electron density of the central metal and $CO_2$ uptake ability was also checked.

Figure 6:
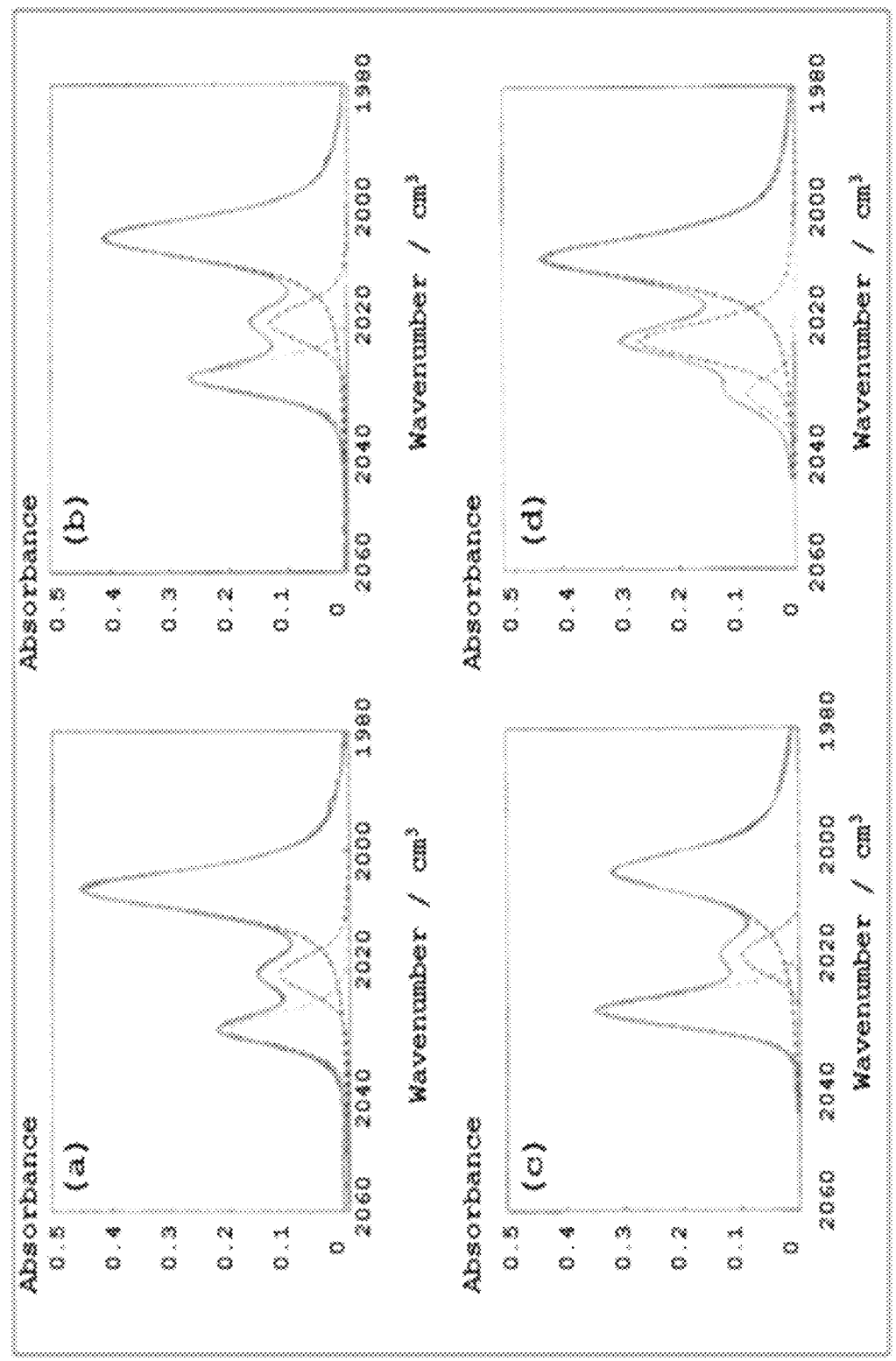
FIG. 6 illustrates IR spectra (black solid lines) obtained after passage of the ambient air and curve fitting curves. (Peaks corresponding to a complex in which DMF is coordinated, a complex in which —O—CO—$OCH_2CH_2NR^2$ (R=$CH_2CH_2OH$) is coordinated, and a complex in which TEOA is coordinated, arranged in this order from a right peak illustrated with a dotted line. A gray solid line is formed by adding up these three peaks.) Substituents in 4,4'-position: (a) hydrogen, (b) a methyl group, (c) a methoxy group, and (d) a bromo group

Re-MeCN, Re((Me)MeCN, Re(MeO)MeCN and Re(Br) MeCN respectively containing a bpy ligand in which hydrogen, a methyl group, a methoxy group or a bromo group was substituted in the 4,4'-position were synthesized. Each of these complexes was dissolved in DMF, the resultant was allowed to stand still in a dark place under Ar atmosphere overnight, and then, TEOA was added thereto, the resultant was allowed to stand still in a dark place under Ar atmosphere for 2 hours, and thus, a DMF-TEOA mixed solution (5:1 v/v) containing the complex in which DMF or TEOA was coordinated was prepared. Change in the IR spectrum caused by allowing the ambient air to pass through each of such solutions for 1 to 2 hours by using a diaphragm pump was observed. Besides, curve fitting analysis was performed in a range of 2060 to 1980 cm$^{-1}$ so as to separate peaks of the respective complexes. FIG. 6 illustrates both the IR spectra and curve fitting curves of the respective solutions.

As a result, it was found that in all of the rhenium complexes containing any one of the bpy ligands, a part of each complex having TEOA coordinated therein took in $CO_2$ contained in the passing air. Besides, 10 to 30% of all the rhenium complexes took $CO_2$ from the ambient air. These results reveal that a rhenium complex works as a good $CO_2$ absorbent. Furthermore, since a gas containing water vapor was allowed to pass, it was predicted that water was unavoidably supplied to the solution and hence generation of Re—OH and Re—OCO$_7$H might compete. After the ambient air was allowed to pass, however, no yellow solid was separated, and hence, it is presumed that none of these complexes were generated or their amounts was ignorably small.

It was found that $CO_2$ uptake efficiency is largely varied depending on a substituent contained in the bpy ligand and that the equilibrium thereof accords with Hammett rule. A positive correlation ($\rho$=0.8>0) was found in a Hammett plot, and it was found that the CO, uptake by Re-TEOA tends to more easily occur as the charge density of rhenium is smaller.

Besides, 1% $CO_2$ or 10% $CO_2$ was allowed to pass instead of the 100% $CO_2$ gas so as to check whether or not $CO_2$ could be taken in by Re-TEOA, and as a result, it was found that $CO_2$ was taken in at high frequency and that a similar compound, Re(bpy)(CO) 3 (OCOCH$_2$CH$_2$)N (CH$_2$CH$_2$OH)$_2$ had been generated.

Figure 13:
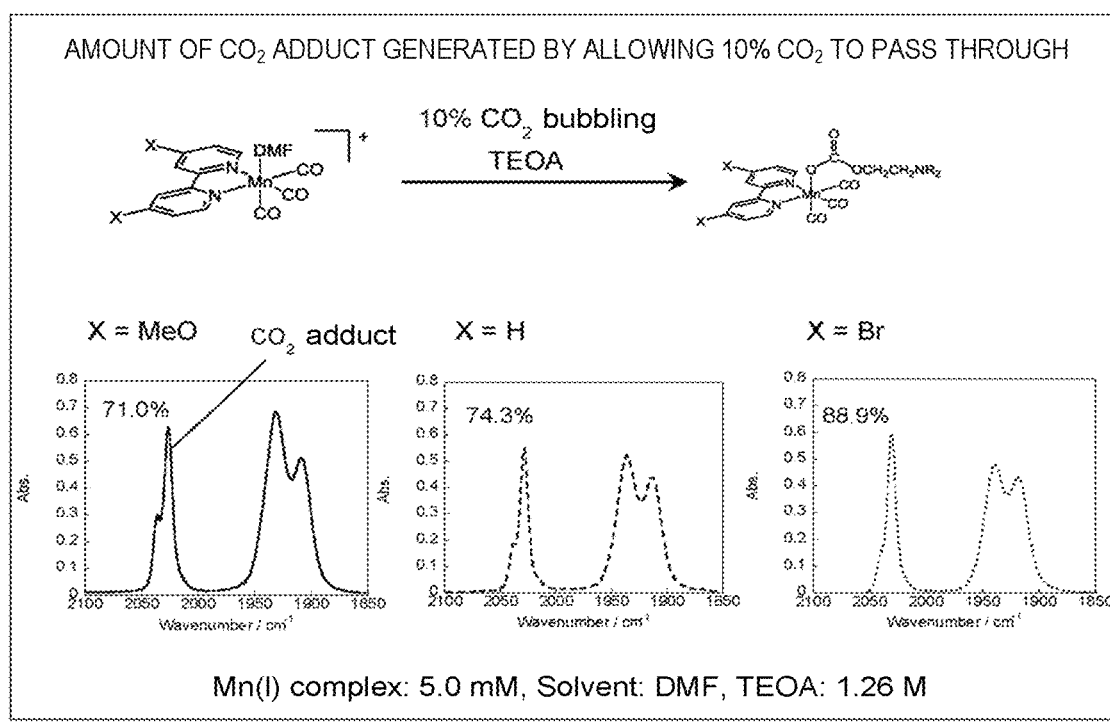
FIG. 13 illustrates IR spectra of various manganese triethanolamine adduct complexes with a $CO_2$ concentration of 10%.

(4) Each of Mn(bpy)(CO)$_3$(MeCN), Mn(MeObpy)(CO)$_3$(MeCN) and Mn(Brbpy)(CO)$_3$(MeCN) was dissolved in DMF containing triethanolamine (TEOA), and $CO_2$ was blown thereinto, so as to examine, through FT-IR measurement, whether or not $CO_2$ was taken in in the same manner as in using the Re complexes (FIG. 13).

As a result, it was found that the following reactions had occurred:

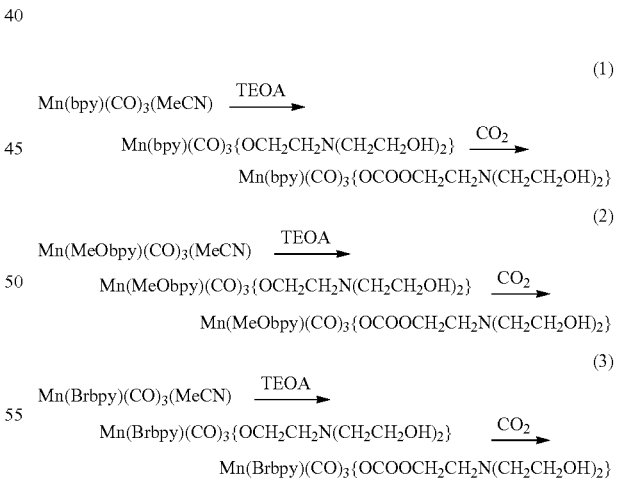

(5) Besides, it was examined whether or not $CO_2$ was taken in even if $CO_2$ at a low concentration was used. The uptake of $CO_2$ was examined by blowing the ambient air instead of $CO_2$. As a result, uptake of 21.7%, 14.7% and 37.1% of $CO_2$ was observed respectively in using Mn(bpy)(CO)$_3${OCH$_2$CH$_2$N(CH$_2$CH$_2$OH)$_2$}, Mn(MeObpy)(CO)$_3${OCH$_2$CH$_2$N(CH$_2$CH$_2$OH)$_2$}, and Mn(Brbpy)(CO)$_3${OCH$_2$CH$_2$N(CH$_2$CH$_2$OH)$_2$}.

(6) Besides, 1% $CO_2$, 2% $CO_2$, 5% $CO_2$ or 10% $CO_2$ was allowed to pass through instead of 100% $CO_2$ gas, and the $CO_2$ uptake by $Mn(bpy)(CO)_3(OCH_2CH_2NH(CH_2CH_2OH)_2)$, $Mn(MeObpy)(CO)_3(OCH_2CH_2N(CH_2CH_2OH)_2)$ or $Mn(Brbpy)(CO)_3(OCH_2CH_2N(CH_2CH_2OH)_2)$ was examined. As a result, it was found, as shown in Table 1, that $CO_2$ was efficiently taken in.

TABLE 1

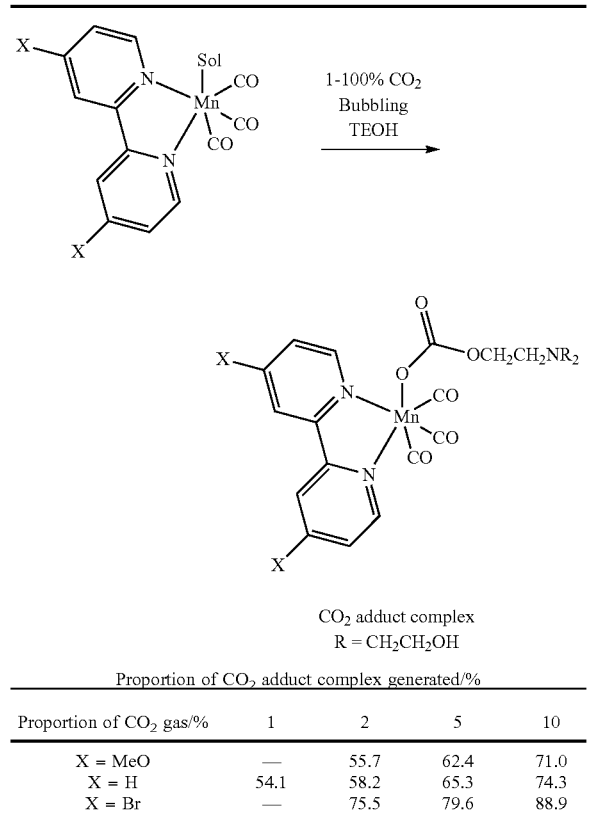

| Proportion of $CO_2$ adduct complex generated/% | | | | |
|---|---|---|---|---|
| Proportion of $CO_2$ gas/% | 1 | 2 | 5 | 10 |
| X = MeO | — | 55.7 | 62.4 | 71.0 |
| X = H | 54.1 | 58.2 | 65.3 | 74.3 |
| X = Br | — | 75.5 | 79.6 | 88.9 |

(7) The $CO_2$ uptake by a Mn complex in which another compound was coordinated instead of triethanolamine was examined.

A Mn complex $(Mn(bpy)(CO)_3(CH_3CN))$ was dissolved in DMF-TEA (triethylamine), and $CO_2$ was blown into the resultant. As a result, $Mn(bpy)(CO)_3(OEt)$ was generated, and a $CO_2$ adduct of this, that is, $Mn(bpy)(CO)OC(O)OEt$, was found to be generated.

(8) The $CO_2$ uptake by a Mn complex in which diethanolamine (DEOA) was coordinated instead of triethanolamine was examined.

Figure 14:
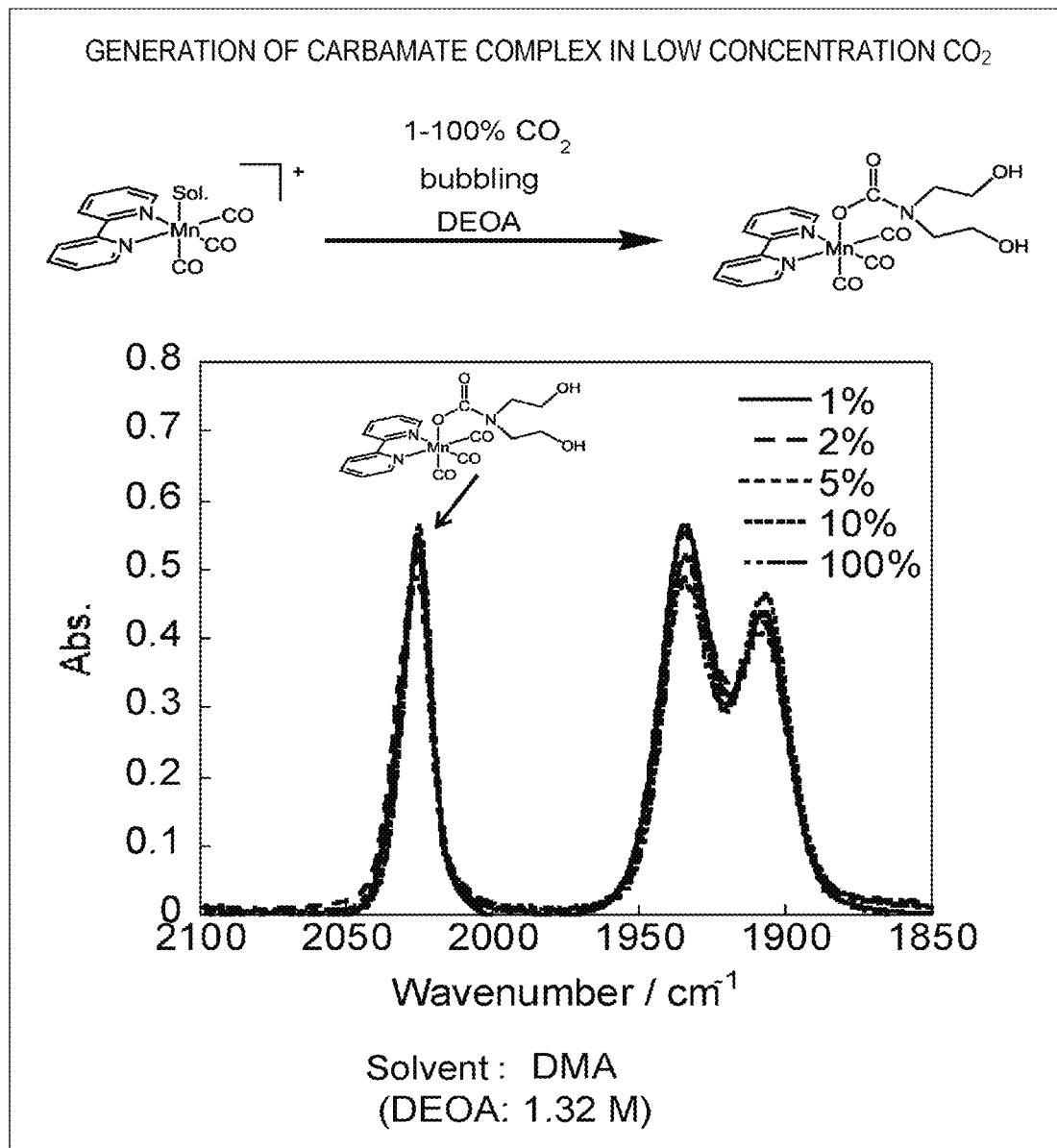
FIG. 14 illustrates IR spectrum change obtained in DMF-DEOA of a Mn complex under atmosphere of various $CO_2$ concentrations.

When a Mn complex was dissolved in a DMF-DEOA mixed solution and $CO_2$ was blown into this solution, a reaction with DEOA present in the solution was caused to generate carbamic acid, and it was found that a carbamate complex $Mn(bpy)(CO)_3(OCON(CH_2CH_2OH)_2)$ was generated through coordination of the carbamic acid in the complex. FIG. 14 illustrates IR spectrum change of the Mn complex in DMF-DEOA under $CO_2$ atmosphere at various concentrations.

(9) The $CO_2$ uptake by a Mn complex in which diethylamine (DEA) was coordinated instead of triethanolamine was examined.

As a result, $Mn(bpy)(CO)_3(DEA)$ was generated from $Mn(bpy)(CO)_3(CH_3CN)$, and a $CO_2$ adduct of this, that is, $Mn(bpy)(CO)_3(OCON(Et)_2)$, was confirmed to be generated.

(10) The $CO_2$ uptake by a Re complex in which another compound was coordinated instead of triethanolamine was examined.

DEOA (diethanolamine) was caused to work on a Re complex $(Re(bpy)(CO)_3(CH_3CN))$ in DMF, and $CO_2$ was blown into the resultant. As a result, $Re(bpy)(CO)_3(NH(CH_2CH_2OH)_2)$ was generated, and a $CO_2$ adduct of this, that is, $Re(bpy)(CO)_3(OCON(CH_2CH_2OH)_2)$, was found to be generated.

(11) The $CO_2$ uptake by a Re complex $(Re(bpy)(CO)_3(CH_3CN))$ in which diethylamine (DEA) was coordinated) was examined.

As a result, $Re(bpy)(CO)_3(DEA)$ was generated from $(Re(bpy)(CO)_3(CH_3CN))$, and a $CO_2$ adduct of this, that is, $Re(bpy)(CO)_3(OCON(Et)_2)$, was confirmed to be generated.

Test Example 1 (Generation of CO Through Electrochemical Reduction Using Re Complex)

Figure 9:
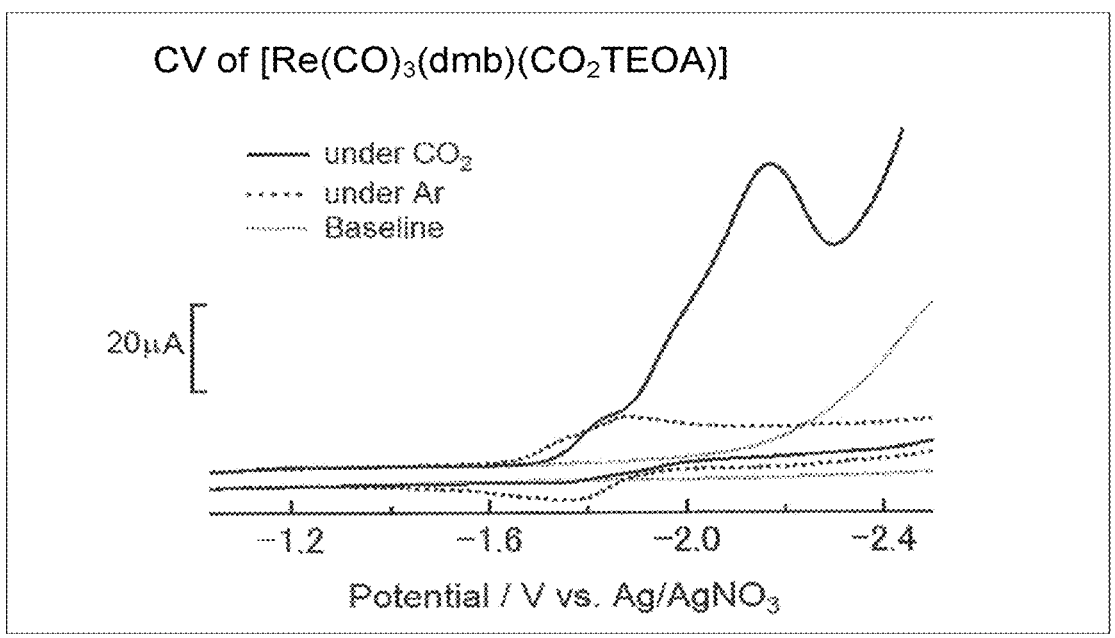
FIG. 9 illustrates measurement results of cyclic voltammetry (CV) of a Re complex performed for setting an application voltage. In this drawing, "baseline" corresponds to a measurement result obtained without the complex under $CO_2$ atmosphere, "under Ar" corresponds to a measurement result obtained with or without the complex under Ar atmosphere, and "under $CO_2$" corresponds to a measurement result obtained with or without the complex under $CO_2$ atmosphere.

An H-type electrochemical cell including an ion exchange membrane (Nafiion-H) disposed inside as schematically illustrated in FIGS. 1 and 2 was produced. On a working electrode side, 84 mL of a DMF-TEOA (in a volume ratio of 5:1) solution containing 0.5 mM $Re(4,4'-(Me)_2(bpy)(CO)_3OCOOCH_2CH_2N(CH_2CH_2OH)_2)$ and 0.1 M $Et_4NBF_4$ was added. On the other hand, on a counter electrode side, 84 mL of a DMF-TEOA (in a volume ratio of 5:1) solution containing 0.1 M $Et_4NBF_4$ was added. Netted glassy carbon (glassy carbon) was used as a working electrode, a platinum cross mesh electrode was used as a counter electrode, and a silver/silver nitrate electrode was used as a reference electrode. FIG. 9 illustrates results of cyclic voltammetry measurement performed for setting an application voltage in this Test Example 1. Based on FIG. 9, a conspicuous current response was found in the vicinity of an application voltage of −2.0 V, and it is determined that a catalytic reduction reaction of $CO_2$ occurred at this voltage.

Figure 7:
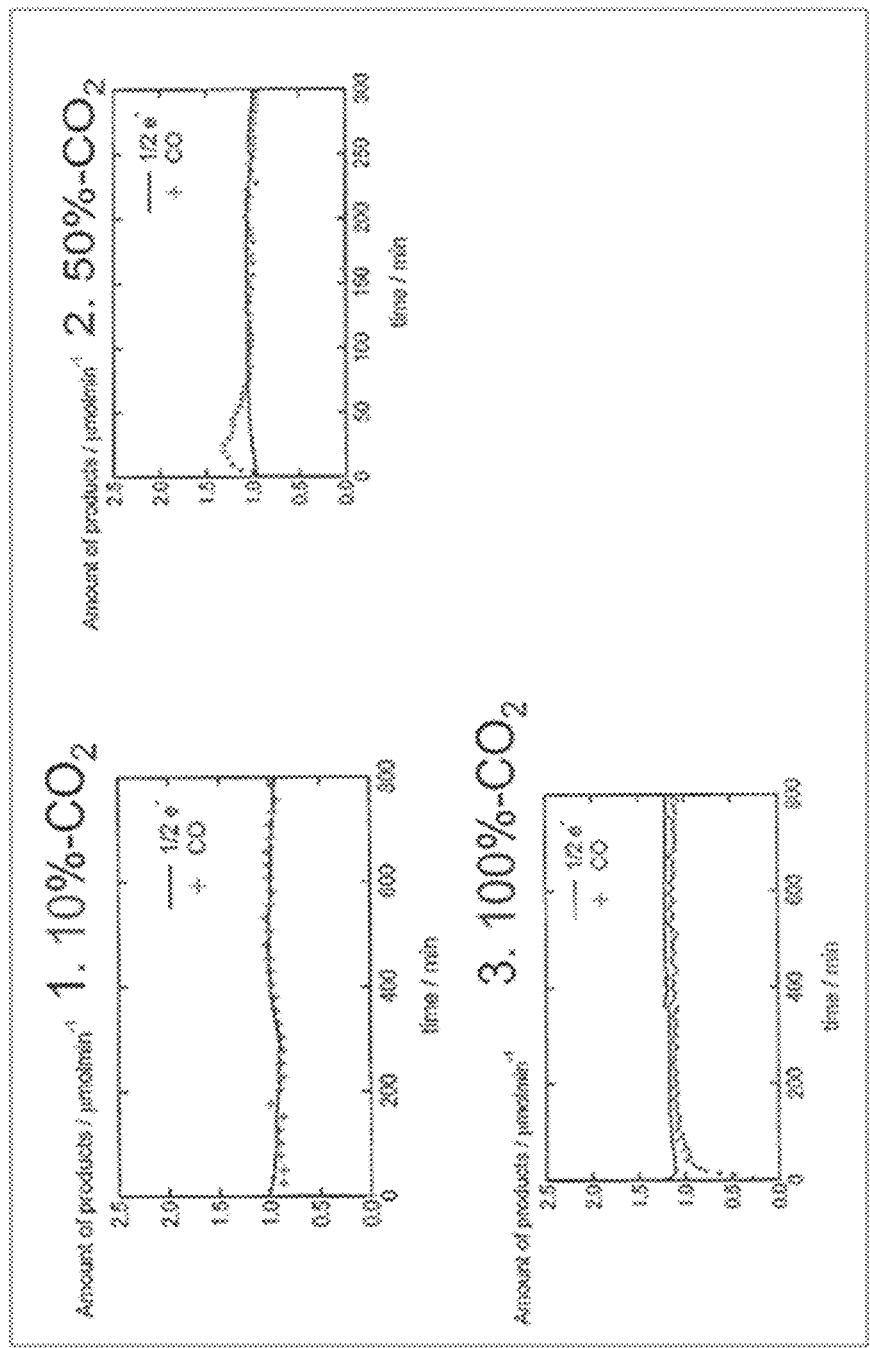
FIG. 7 illustrates amount of CO generated and current change obtained in electrochemical $CO_2$ reduction experiment using Re—$CO_2$-TEOA as a catalyst.

On the working electrode side, 10% $CO_2$, 50% $CO_2$ or 100% $CO_2$ (a component excluding $CO_2$ being Ar) was bubbled, and a voltage of −2.1 V (using $Ag/AgNO_3$ as the reference electrode) was applied. As a result, it was found, as illustrated in FIG. 7, that $CO_2$ was selectively reduced to CO even if the $CO_2$ concentration was 10%. The faradaic efficiency of the CO generation was substantially 100%.

Test Example 2

An electrochemical cell similar to that of Test Example 1 except that the solvent DMF-TEOA used on the working electrode side was changed to DMF was produced. While bubbling 10% $CO_2$ gas, 7 mL of TEOA was added on the working electrode side, and change in a current at which CO was generated was observed.

Figure 8:
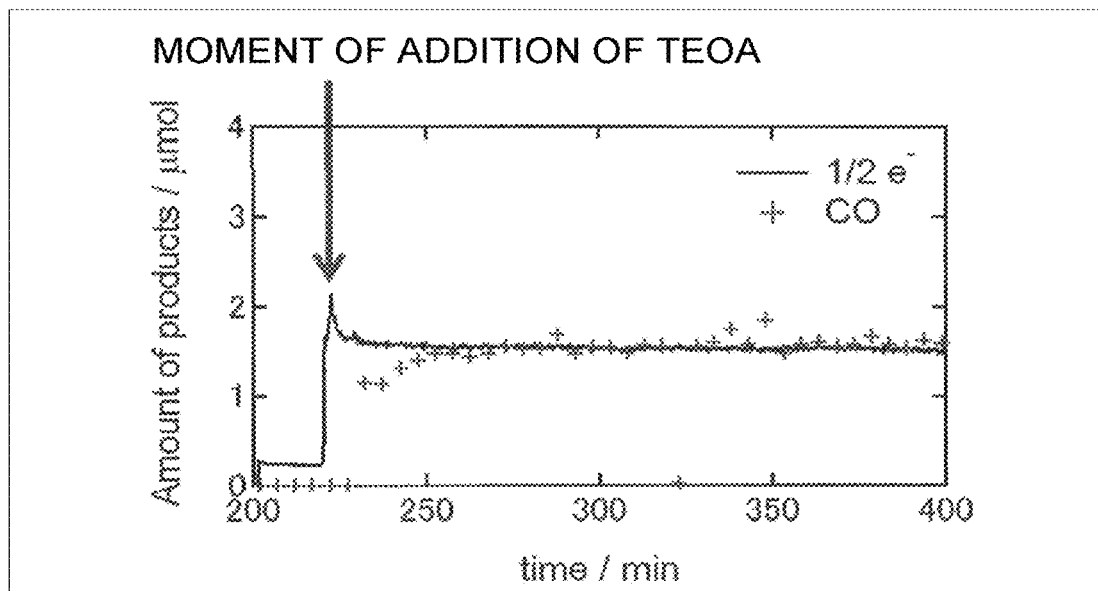
FIG. 8 illustrates amount of CO generated and current change obtained by adding TEOA.

As a result, as illustrated in FIG. 8, the current value was increased by about 6 times from 0.76 mA to 4.85 mA, and it was understood that $CO_2$ reducing ability could be further improved by causing $CO_2$ addition function (by shifting the equilibrium relationship toward side of generation of a $CO_2$ adduct) through addition of TEOA.

Test Example 3 (Generation of Formic Acid Through Electrochemical Reduction Using Mn Complex and TEOA)

Figure 10:
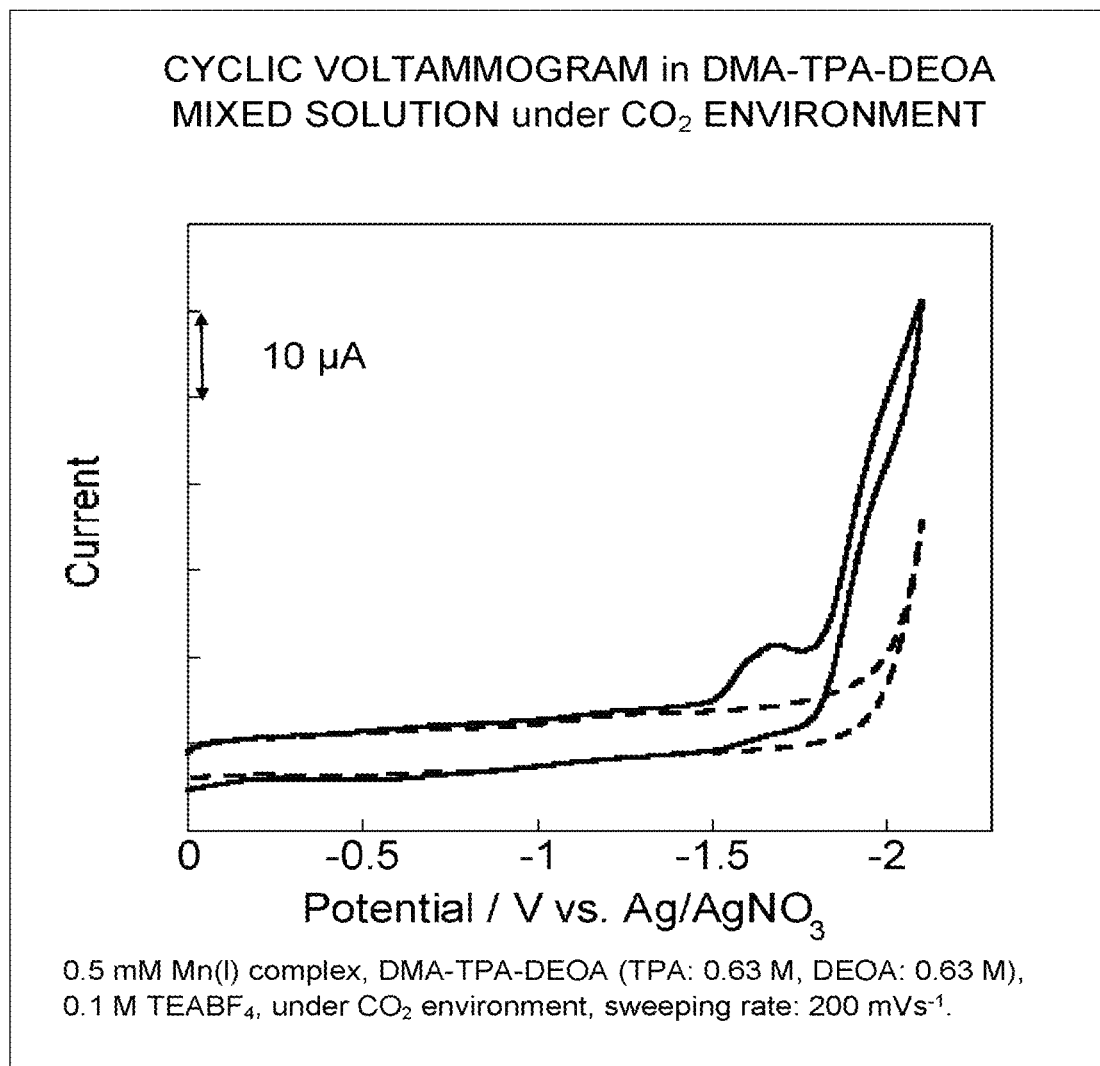
FIG. 10 illustrates measurement results of the cyclic voltammetry (CV) of a Mn complex performed for setting an application voltage. A dotted line corresponds to a result obtained under Ar atmosphere. A solid line corresponds to a result obtained under $CO_2$ atmosphere.
Figure 11:
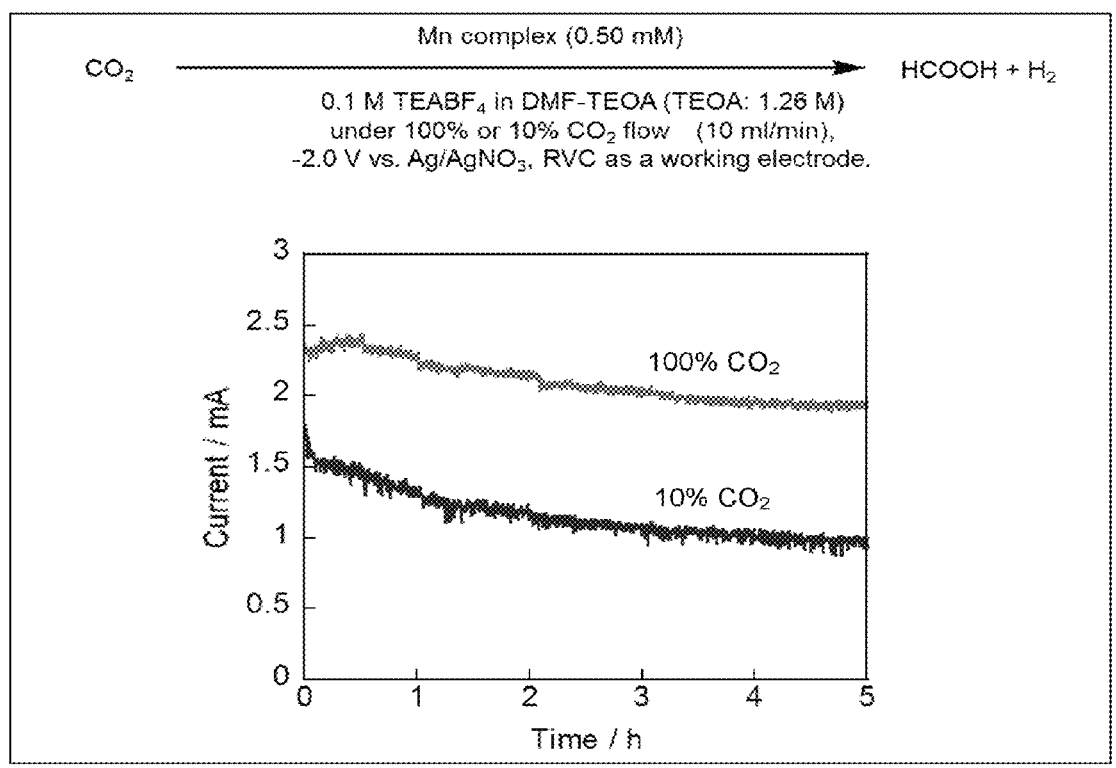
FIG. 11 illustrates current value change obtained in an electrochemical $CO_2$ reduction experiment using Mn—$CO_2$-TEOA as a catalyst.

An H-type electrochemical cell including an ion exchange membrane (Nafiion-H) disposed inside was produced. On a working electrode side, 84 mL of a DMF-TEOA solution (TEOA: 1.26 M) containing 0.5 mM Mn(bpy)(CO)$_3$ OCOOCH$_2$CH$_2$N(CH$_2$CH$_2$OH)$_2$ and 0.1 M TEABF$_4$ was added. On the other hand, on a counter electrode side, 84 mL of a DMF-TEOA solution (TEOA: 1.26 M) containing 0.1 M TEABF$_4$ was added. Netted glassy carbon (glassy carbon) was used as a working electrode, a platinum cross mesh electrode was used as a counter electrode, and a silver/silver nitrate electrode was used as a reference electrode. FIG. 10 illustrates results of the cyclic voltammetry measurement performed for setting an application voltage in this Test Example 3. Based on FIG. 10, a conspicuous current response was found in the vicinity of an application voltage of −2.0 V, and it is determined that a catalytic reduction reaction of CO$_2$ occurred at this voltage.

Figure 12:
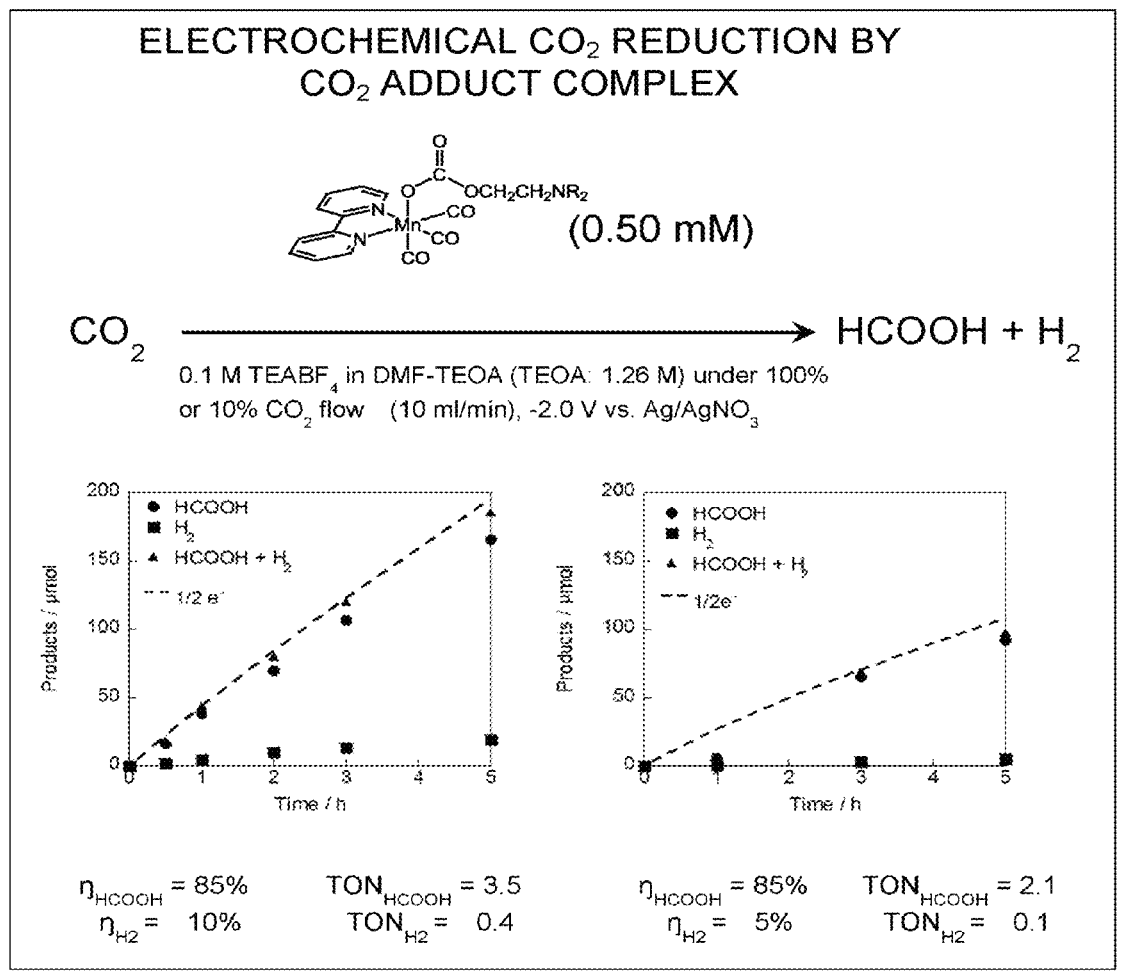
FIG. 12 illustrates amount of CO generated obtained in the electrochemical $CO_2$ reduction experiment using Mn—$CO_2$-TEOA as a catalyst.

On the working electrode side, 10% CO$_2$ or 100% CO$_2$ (a component excluding CO$_2$ being Ar) was bubbled, and a voltage of 2.0 V (using Ag/AgNO$_3$ as the reference electrode) was applied. As a result, it was found, as illustrated in FIGS. 12 and 13, that formic acid was selectively generated even if the CO$_2$ concentration was 10%.

Test Example 4 (Generation of Formic Acid Through Electrochemical Reduction Using Mn Complex and DEOA)

Figure 15:
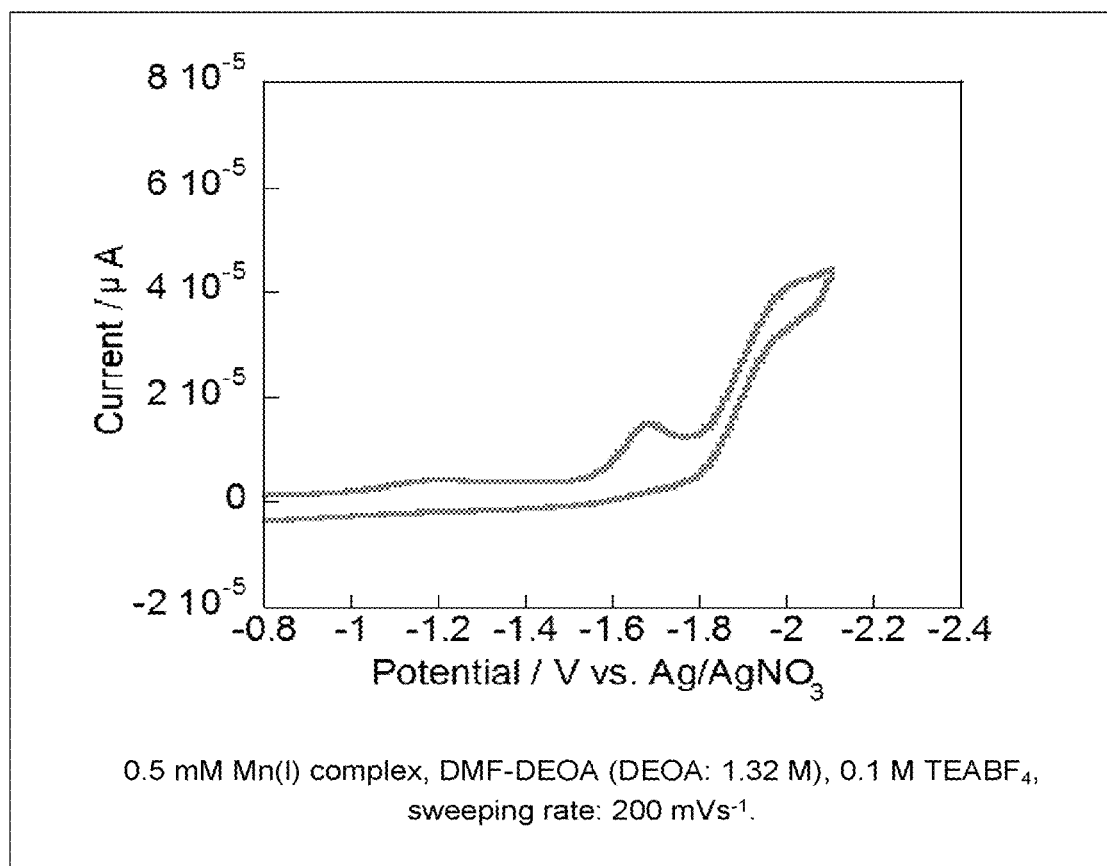
FIG. 15 illustrates measurement results of the cyclic voltammetry (CV) of a Mn complex in DMF-DEOA under $CO_2$ atmosphere performed for setting an application voltage.
Figure 16:
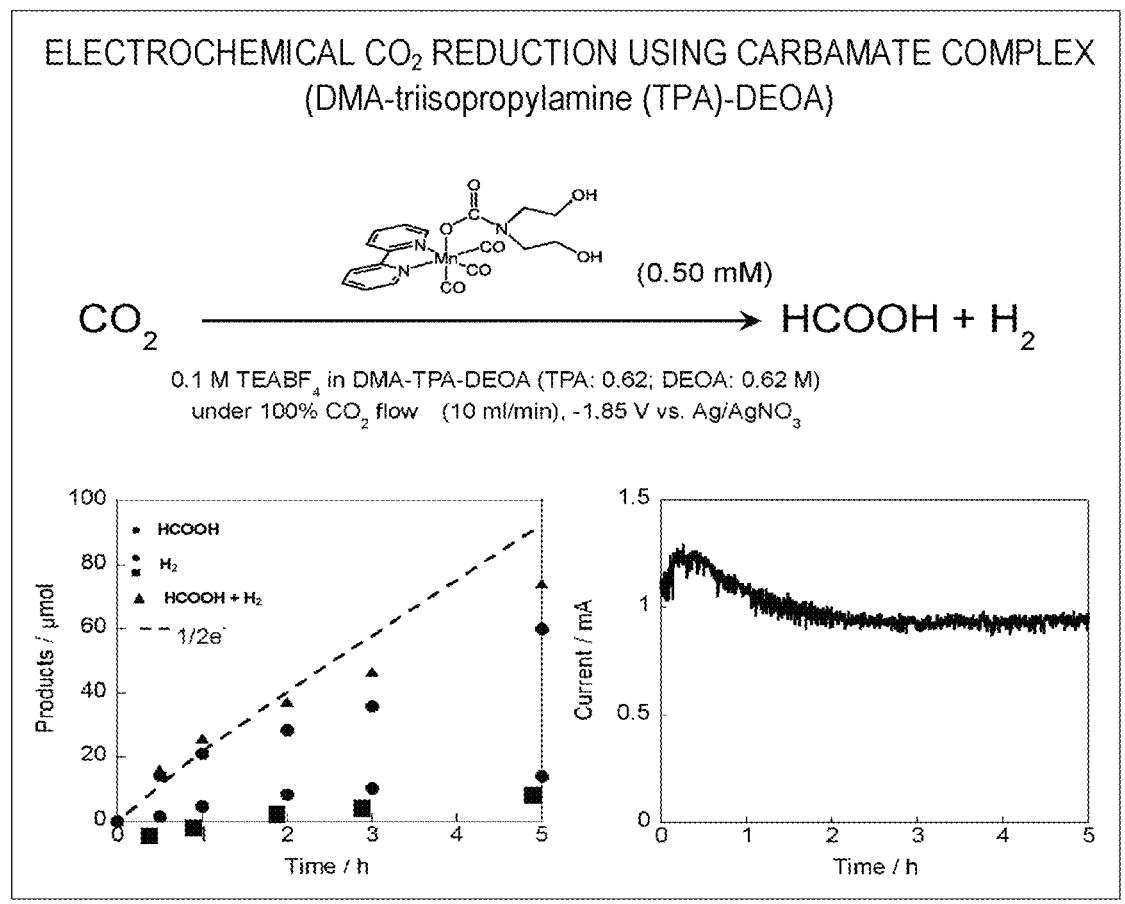
FIG. 16 illustrates amount of formic acid generated and current value change obtained in an electrochemical $CO_2$ reduction experiment using Mn—$CO_2$-DEOA as a catalyst.

An H-type electrochemical cell including an ion exchange membrane (Nafiion-H) disposed inside was produced. On a working electrode side, 95 mL of a DMF solution containing 0.5 mM Mn(bpy)(CO)$_3$(OCONCH$_2$CH$_2$NR$_2$) (R =CH$_2$CH$_2$OH), 0.1 M Et$_4$NBF$_4$, 0.62 M DEOA and 0.62 M tripropylamine was added. On a counter electrode side, 95 mL of a DMF solution containing 0.1 M Et$_4$NBF$_4$, 0.62 M DEOA and 0.62 M tripropylamine was added. Netted glassy carbon was used as a working electrode, a platinum mesh electrode was used as a counter electrode, and a silver/silver nitrate electrode was used as a reference electrode. FIG. 15 illustrates results of the cyclic voltammetry measurement performed for setting an application voltage in this Test Example 4. Based on FIG. 15, a conspicuous current response was found in the vicinity of an application voltage of −1.85 V, and it is determined that a catalytic reduction reaction of CO$_2$ occurred at this voltage.

While bubbling CO$_2$ gas on the working electrode side, a voltage of −1.85 V (using Ag/AgNO$_3$ as the reference electrode) was applied. As a result, it was found that CO$_2$ was highly selectively reduced to HCOOH.

The invention claimed is:

1. A method for producing formic acid by electrochemically reducing carbon dioxide, the method comprising: (a) reacting carbon dioxide with a metal complex represented by formula (2a) to obtain a reaction product:

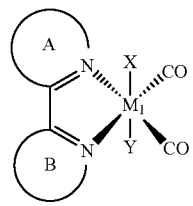

(2a)

wherein M$_1$ represents, ruthenium or iron,
X represents O(CH$_2$)$_n$NR$^5$R$^6$, NR$^5$R$^6$, or PX$^1$X$^2$X$^3$,
Y represents CO, O(CH$_2$)$_n$NR$^5$R$^6$, NR$^5$R$^6$, or PX$^1$X$^2$X$^3$,
ring A and ring B form a nitrogen-containing heterocycle having a 2,2'-bipyridine structure optionally having one to four substituents, each independently selected from the group consisting of an alkyl group, an alkoxy group, an aryloxy group and a halogen atom,
R$^5$ and R$^6$ are identical or different and represent an alkyl group, a hydroxyalkyl group or a hydrogen atom,
n represents a number of 2 to 8, and
one, two or three of X$^1$, X$^2$ and X$^3$ are identical or different and represent a hydrocarbon group optionally having a substituent or a hydrocarbon oxy group optionally having a substituent, the rest representing a hydrogen atom or a hydroxy group; and
(b) applying a voltage to the reaction product.

2. The production method according to claim 1, wherein (a) and (b) are performed within an electrochemical cell including a working electrode and a counter electrode, and the method further comprises:
(a1) introducing carbon dioxide into a solution containing the metal complex held in the electrochemical cell; and
(b1) applying a negative voltage and a positive voltage respectively to the working electrode and the counter electrode of the electrochemical cell.

3. The production method according to claim 2, wherein the carbon dioxide is introduced by introducing a carbon dioxide-containing gas into the solution containing the metal complex.

4. The production method according to claim 1, wherein the carbon dioxide to be reacted is in the form of a gas containing 0.03 to 100% of carbon dioxide.

5. The production method according to claim 1, wherein each of X$^1$, X$^2$ and X$^3$ is independently one selected from the group consisting of an alkyl group, an alkenyl group, a cycloalkyl group, a cycloalkenyl group and an aromatic hydrocarbon group, each of which optionally has one to three substituents selected from the group consisting of a primary, secondary or tertiary amino group, a hydroxy group, an alkoxy group, an aryloxy group, a halogen atom, a nitro group, a cyano group, a formyl group, an alkanoyl group and an arylcarbonyl group.

* * * * *